US011653828B2

(12) United States Patent
Bagherinia

(10) Patent No.: US 11,653,828 B2
(45) Date of Patent: May 23, 2023

(54) SYSTEMS AND METHODS FOR IMPROVED ANTERIOR SEGMENT OCT IMAGING

(71) Applicant: Carl Zeiss Meditec, Inc., Dublin, CA (US)

(72) Inventor: Homayoun Bagherinia, Oakland, CA (US)

(73) Assignee: Carl Zeiss Meditec, Inc., Dublin, CA (US)

( * ) Notice: Subject to any disclaimer, the term of this patent is extended or adjusted under 35 U.S.C. 154(b) by 137 days.

(21) Appl. No.: 17/171,857

(22) Filed: Feb. 9, 2021

(65) Prior Publication Data

US 2021/0177253 A1    Jun. 17, 2021

Related U.S. Application Data

(62) Division of application No. 15/639,302, filed on Jun. 30, 2017, now Pat. No. 10,952,603.

(Continued)

(51) Int. Cl.
*G06K 9/00* (2022.01)
*A61B 3/00* (2006.01)
(Continued)

(52) U.S. Cl.
CPC .......... *A61B 3/0025* (2013.01); *A61B 3/0008* (2013.01); *A61B 3/0041* (2013.01); *A61B 3/102* (2013.01); *A61B 5/7207* (2013.01); *G06T 5/003* (2013.01); *G06T 5/50* (2013.01); *G06T 7/0012* (2013.01); *G06T 7/215* (2017.01); *G06T 7/33* (2017.01); *A61B 5/7225* (2013.01);
(Continued)

(58) Field of Classification Search
None
See application file for complete search history.

(56) References Cited

U.S. PATENT DOCUMENTS 7,365,856 B2 * 4/2008 Everett ............... A61B 5/0059
250/227.27
7,452,077 B2   11/2008 Meyer et al.
(Continued)

OTHER PUBLICATIONS

Blazkiewicz et al., (2005). "Signal-To-Noise Ratio Study of Full-Field Fourier-Domain Optical Coherence Tomography," Applied Optics, 44(36):7722-7729.
(Continued)

*Primary Examiner* — Avinash Yentrapati
(74) *Attorney, Agent, or Firm* — Snell & Wilmer L.L.P.

(57) ABSTRACT

Various methods and systems for improved anterior segment optical coherence tomography (OCT) imaging are described. One example method includes collecting a set of B-scans over a range of different transverse locations on the cornea, segmenting each B-scan to identify an anterior corneal layer and an outer edge of Bowman's layer, calculating thickness values for each B-scan by computing the distance from the anterior corneal layer to the outer edge of the Bowman's layer, combining the thickness values from the B-scans to create a polar epithelial thickness map, converting the polar epithelial thickness map to a Cartesian epithelial thickness map using a fitting method, and storing or displaying the Cartesian epithelial thickness map or information derived from the Cartesian epithelial thickness map.

22 Claims, 13 Drawing Sheets
(5 of 13 Drawing Sheet(s) Filed in Color)

Related U.S. Application Data

(60) Provisional application No. 62/384,974, filed on Sep. 8, 2016, provisional application No. 62/361,651, filed on Jul. 13, 2016.

(51) Int. Cl.

| | | |
|---|---|---|
| *A61B 3/10* | (2006.01) | |
| *A61B 5/00* | (2006.01) | |
| *G06T 7/215* | (2017.01) | |
| *G06T 5/50* | (2006.01) | |
| *G06T 7/00* | (2017.01) | |
| *G06T 5/00* | (2006.01) | |
| *G06T 7/33* | (2017.01) | |

(52) U.S. Cl.
CPC ............... *G06T 2207/10101* (2013.01); *G06T 2207/20201* (2013.01); *G06T 2207/20212* (2013.01); *G06T 2207/30041* (2013.01); *G06T 2207/30168* (2013.01)

(56) References Cited

U.S. PATENT DOCUMENTS

| | | | |
|---|---|---|---|
| 7,878,651 B2 | 2/2011 | O'Hara et al. | |
| 9,101,294 B2 | 8/2015 | Bagherinia et al. | |
| 9,332,902 B2 * | 5/2016 | Tumlinson | G01B 9/02043 |
| 9,706,914 B2 * | 7/2017 | Bagherinia | A61B 3/0025 |
| 2007/0282313 A1 * | 12/2007 | Huang | A61F 9/00831 |
| | | | 606/5 |
| 2007/0291277 A1 * | 12/2007 | Everett | G01B 9/02077 |
| | | | 356/497 |
| 2008/0055543 A1 * | 3/2008 | Meyer | A61B 3/113 |
| | | | 351/205 |
| 2008/0170204 A1 * | 7/2008 | Podoleanu | G01B 9/02028 |
| | | | 356/516 |
| 2009/0168017 A1 * | 7/2009 | O'Hara | A61B 5/0073 |
| | | | 351/205 |
| 2011/0032533 A1 * | 2/2011 | Izatt | G06T 5/006 |
| | | | 356/497 |
| 2013/0012822 A1 | 1/2013 | Gamelin et al. | |
| 2013/0188140 A1 * | 7/2013 | Bagherinia | G01B 9/02077 |
| | | | 351/246 |
| 2015/0133901 A1 * | 5/2015 | Serdarevic | A61N 7/00 |
| | | | 606/5 |
| 2016/0038021 A1 * | 2/2016 | Bagherinia | G01B 9/02083 |
| | | | 351/246 |
| 2017/0035286 A1 * | 2/2017 | Meyer | A61B 3/0025 |

OTHER PUBLICATIONS

Choma et al., (2003). "Sensitivity Advantage of Swept Source and Fourier Domain Optical Coherence Tomography," Optics Express, 11(18):2183-2189.

D'Errico, John R.," Understanding Gridfit," woodchips@rochester.rr.com, Dec. 28, 2006, 6 pages.

De Boer et al., (2003). "Improved Signal-to-Noise Ratio in Spectral-Domain Compared with Time-Domain Optical Coherence Tomography," Optics Letters, 28(21):2067-2069.

Fischler et al., (1981). "Random Sample Consensus: A Paradigm for Model Fitting with Applications to Image Analysis and Automated Cartography," Communications of the ACM, 24(6):381-395.

Hillmann et al., (2011). "Holoscopy-Holographic Optical Coherence Tomography," Optics Letters, 36(13):2390-2392.

Leitgeb et al., (2003). "Performance of Fourier Domain vs. Time Domain Optical Coherence Tomography," Optics Express, 11(8):889-894.

Li et al., (2008). "Keratoconus Diagnosis with Optical Coherence Tomography Pachymetry Mapping," Ophthalmology, 115(12):2159-2166.

Li et al., (2010). "Pachymetric Mapping with Fourier-Domain Optical Coherence Tomography," Journal of Cataract and Refractive Surgery, 36:826-831.

Nakamura et al., (2007). "High-Speed Three-Dimensional Human Retinal Imaging by Line-Field Spectral Domain Optical Coherence Tomography," Optics Express, 15(12):7103-7116.

Reinstein et al., (2009). "Corneal epithelial thickness profile in the diagnosis of keratoconus," J Refract Surg., 25(7):604-610.

Tang et al., (2006). "Measuring Total Corneal Power Before and After Laser In Situ Keratomileusis with High-Speed Optical Coherence Tomography," Journal of Cataract and Refractive Surgery, 32:1843-1850.

Tang et al., (2010). "Corneal Power Measurement With Fourier-domain Optical Coherence Tomography," Journal of Cataract and Refractive Surgery, 36:2115-2122.

Telea, (2004). "An Image Inpainting Technique Based on the Fast Marching Method," Journal of Graphics Tools, 9(1):3-34.

Timp et al., (2004). "A new 2d Segmentation Method Based on Dynamic Programming Applied to Computer Aided Detection in Mammography," Medical Physics, 31(5):958-971.

Zhu et al., (2007). "L-BFGS-B: Algorithm 778: L-BFGS-B Fortran Routines for Large Scale Bound Constrained Optimization," ACM Transactions on Mathematical Software, 23(4):550-560.

\* cited by examiner

SYSTEMS AND METHODS FOR IMPROVED ANTERIOR SEGMENT OCT IMAGING

PRIORITY

This application is a divisional of U.S. patent application Ser. No. 15/639,302, filed Jun. 30, 2017 which in turn claimed priority to Provisional Application Ser. No. 62/361,651, filed Jul. 13, 2016, and Provisional Application Ser. No. 62/384,974, filed Sep. 8, 2016, the contents of all of which are hereby incorporated by reference in their entirety.

FIELD OF THE INVENTION

The present application relates to the field of optical coherence tomography (OCT), and in particular, systems and methods of improved OCT imaging of the cornea.

BACKGROUND

Optical coherence tomography (OCT) is an optical imaging technology for performing in situ real-time cross-sectional imaging of tissue structures at a resolution of less than 10 microns. OCT measures the scattering profile of a sample along the OCT beam. Each scattering profile is called an axial scan, or A-scan. Cross-sectional images, called B-scans, and by extension 3D volumes, are built up from many A-scans, with the OCT beam illuminating to a set of transverse locations on the sample either by scanning or field illumination.

It has been demonstrated that Fourier domain OCT (FD-OCT) has advantages over the original time-domain OCT (TD-OCT) (see for example, R. A. Leitgeb et al. (2003). "Performance of fourier domain vs. time domain optical coherence tomography." Optics Express 11(8): 889-94; J. F. de Boer et al. (2003). "Improved signal-to-noise ratio in spectral-domain compared with time-domain optical coherence tomography." Optics Letters 28(21): 2067-2069; M. A. Choma et al. (2003). "Sensitivity advantage of swept source and Fourier domain optical coherence tomography." Optics Express 11(18): 2183-89). In TD-OCT, the optical path length between the sample and reference arms needs to be mechanically scanned. In FD-OCT, on the other hand, the optical path length difference between the sample and reference arm is not mechanically scanned. Instead, a full A-scan is obtained in parallel for all points along the sample axial line within a short time, determined by the wavelength sweep rate of a swept source in swept-source OCT (SS-OCT) or the line scan rate of the line scan camera in spectral-domain OCT (SD-OCT). As a result, the speed for each axial scan can be substantially increased as compared to the mechanical scanning speed of TD-OCT.

Even with the increased speed of FD-OCT, however, the accuracy of OCT for a number of ophthalmic applications can be limited by the effects of eye motion during data acquisition. These applications include pachymetry (i.e., measurement of corneal thickness), keratometry (i.e., measurement of the curvature of the anterior surface of the cornea), corneal power calculations, epithelial thickness mapping, and corneal topography. The quality of the data affects the performance of algorithms that generate measurements. These algorithms include corneal motion correction, corneal layers segmentation, epithelial mapping, etc. Corneal motion correction may be necessary due to poor fixation targets, poor fixators, and longer scan times (e.g., repeat scans to improve the signal to noise (SNR) and contrast). In some instances, a check of the corneal scan quality may be desirable prior to performing the corneal motion correction to avoid time spent processing sub-optimal data. Some of the factors that could lead to poor quality data include large eye motion in the scan data, inexperienced operator, poor alignment, poor fixation target, and/or poor fixator.

An existing method for correcting the effects of eye motion in corneal scans is described by U.S. Pat. No. 9,101,294, the contents of which are hereby incorporated by reference. This method includes acquiring a first sparse set of data using an OCT system. This first sparse set of data is acquired in a relatively short amount of time (e.g., within a few tens of milliseconds), which can be realized with an ultrafast system having a speed greater than 100 kHz. The first sparse set of data is used to create an initial surface model of the cornea, which is then used to register a second set of more dense data acquisition. From this second set of dense data, a more accurate motion-corrected model of the cornea is created.

The motion-corrected model of the cornea can be used to generate motion-artifact free epithelial thickness maps. An epithelial thickness map is used for analyzing the human corneal epithelium thickness, which can facilitate in the early stage detection of keratoconus. Keratoconus is a progressive eye disease in which the normally round cornea thins and begins to bulge into a cone-like shape. This cone shape deflects light as it enters the eye on its way to the light-sensitive retina, causing distorted vision. Front surface corneal topography is the current standard for keratoconus screening. Epithelial thickness maps can be used as an additional diagnostic tool to improve early detection of keratoconus when corneal topography is uncertain on diagnosis. U.S. Publication No. 2013/0128222 describes a method for measuring the corneal epithelial thickness and generating an epithelial thickness map for keratoconus diagnosis.

Here we describe new and improved methods of 1) motion correction in corneal scans and 2) generating epithelial thickness maps, and 3) scan quality assessment in corneal image data of an eye.

SUMMARY

According to one aspect of the subject matter described in the present application, a method of motion correction in corneal image data of an eye using an optical coherence tomography (OCT) system includes collecting a set of OCT data of the cornea of the eye; segmenting the set of OCT data to identify one or more corneal layers; fitting a two-dimensional model of corneal surfaces to the one or more corneal layers; determining motion-correction parameters by minimizing error between the one or more corneal layers and the two-dimensional model of the corneal surfaces; creating a motion-corrected corneal image dataset from the set of OCT data using the motion-correction parameters; and storing or displaying the motion-corrected corneal image dataset or information derived from the motion-corrected corneal image dataset.

This method of motion correction is particularly advantageous in a number of respects. By way of example and not limitation, (1) the method allows longer scan time (e.g., multiple scans for averaging), (2) it can work with slower OCT systems (e.g., 27 kHz), (3) no need for an additional set of scan data (e.g. sparse scan data) or other modalities (e.g., Placido based corneal topography) as a reference for motion correction and instead takes advantage of natural shape of cornea to be used as the reference, (4) existing scans can be corrected, and (5) optimization convergence is relatively fast (e.g., less than 5 seconds).

According to another aspect of the subject matter described in the present application, a method of analyzing an epithelial layer of a cornea of an eye using an optical coherence tomography (OCT) system includes collecting a set of B-scans over a range of different transverse locations on the cornea of the eye; segmenting each B-scan to identify an anterior corneal layer and an outer edge of Bowman's layer; calculating thickness values, for each B-scan, by computing the distance from the anterior corneal layer to the outer edge of the Bowman's layer; combining the thickness values from the B-scans to create a polar epithelial thickness map; converting the polar epithelial thickness map to a Cartesian epithelial thickness map using a fitting method; and storing or displaying the Cartesian epithelial thickness map or information derived from the Cartesian epithelial thickness map.

The above method of epithelial thickness mapping is particularly advantageous in a number of respects. By way of example and not limitation, (1) there is no need for repeated B-scans to boost the signal to noise ratio (SNR) and contrast (e.g. by registration and averaging), (2) segmentation of outer edge of Bowman's layer is possible in peripheral region despite weak signals, (3) epithelial thickness mapping is possible for a larger field of view (e.g. 9-12 mm), (4) motion correction enables 3-D thickness value calculation.

According to yet another aspect of the subject matter described in the present application, a method of creating a motion-corrected epithelial thickness map of a cornea of an eye using an optical coherence tomography (OCT) system includes collecting a set of OCT data of the cornea of the eye; segmenting the OCT data to identify one or more corneal layers; fitting a two-dimensional model of corneal surfaces to the one or more corneal layers; determining motion-correction parameters by minimizing error between the one or more corneal layers and the two-dimensional model of the corneal surfaces; creating a motion-corrected corneal image dataset from the set of OCT data using the motion-correction parameters; determining epithelial thickness of the cornea from the motion-corrected corneal image dataset; creating an epithelial thickness map based on the determined epithelial thickness of the cornea; and storing or displaying the epithelial thickness map or a further analysis thereof.

According to yet another aspect of the subject matter described in the present application, a method to assess the scan quality of corneal image data of an eye using an optical coherence tomography (OCT) system includes collecting a set of OCT data of the cornea of the eye; segmenting the set of OCT data to identify one or more corneal layers; fitting a two-dimensional model of corneal surfaces to the one or more corneal layers; performing one or more scan quality assessment tests to assess scan quality of collected data based on results of the segmentation and the fitting; determining whether the one or more scan quality assessment tests meet an acceptable scan quality condition; and re-acquiring the bad data or reporting the results of the determination to an operator or a further analysis thereof.

This method of scan quality assessment is particularly advantageous in a number of respects. By way of example and not limitation, the method reports an informative indicator to an operator if any of the following situation occurs (1) poor scan quality (due to blink, partial blink, eyelid/eyelash interference, low contrast, etc.), (2) scan position is too high or too low, (3) vertex is off center, and (4) large motion (e.g., lateral, rotation motion and tilt in scans). Only when the scan quality is acceptable, the scan data is used for performing subsequent operations, such as for example, corneal motion correction, epithelial thickness mapping, etc.

Further aspects include various additional features and operations associated with the above and following aspects and may further include, but are not limited to corresponding systems, methods, apparatus, and computer program products. It should be noted that the above aspects may not be entirely independent and could be used either alone or in combination with each other.

The features described herein are not all-inclusive and many additional features will be apparent to one of ordinary skill in the art in view of the figures and description. Moreover, it should be noted that the language used in the specification has been principally selected for readability and instructional purposes and not to limit the scope of the inventive subject matter.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

All patent and non-patent references cited within this specification are herein incorporated by reference in their entirety to the same extent as if the disclosure of each individual patent and non-patient reference was specifically and individually indicated to be incorporated by reference in its entirely.

Example OCT System

Figure 1:
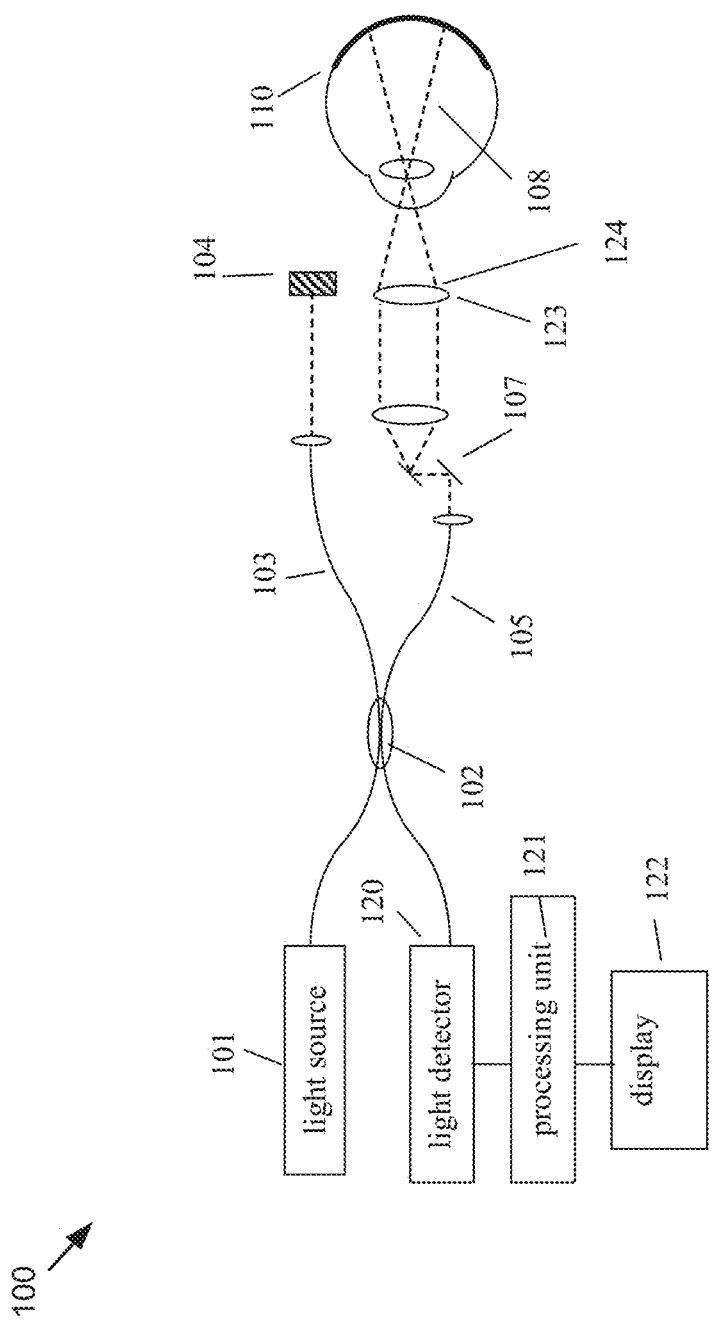
FIG. 1 is a generalized optical coherence tomography (OCT) system that can be used to practice the present invention.

A generalized FD-OCT system used to collect 3-D image data of the eye suitable for use with the present invention is illustrated in FIG. 1. A FD-OCT system 100 includes a light source, 101, typical sources including but not limited to broadband light sources with short temporal coherence lengths or swept laser sources. A beam of light from source 101 is routed, typically by optical fiber 105, to illuminate the sample 110, a typical sample being tissues in the human eye. The source 101 can be either a broadband light source with short temporal coherence length in the case of SD-OCT or a wavelength tunable laser source in the case of SS-OCT. The light is directed towards a region of the sample 110, typically with a scanner 107 between the output of the fiber and the sample, so that the beam of light (dashed line 108) is scanned laterally (in x and y) over the region of the sample to be imaged. Light scattered from the sample is collected, typically into the same fiber 105 used to route the light for illumination. Reference light derived from the same source 101 travels a separate path, in this case involving fiber 103 and retro-reflector 104 with an adjustable optical delay. Those skilled in the art recognize that a transmissive reference path can also be used and that the adjustable delay could be placed in the sample or reference arm of the interferometer. Collected sample light is combined with reference light, typically in a fiber coupler 102, to form light interference in a detector 120. Although a single fiber port is shown going to the detector, those skilled in the art recognize that various designs of interferometers can be used for balanced or unbalanced detection of the interference signal. The output from the detector 120 is supplied to a processor 121 that converts the observed interference into depth information of the sample. The results can be stored in the processor 121 or other storage medium or displayed on display 122. The processing and storing functions may be localized within the OCT instrument or functions may be performed on an external processing unit (e.g., the computer system 900 shown in FIG. 9) to which the collected data is transferred. This unit could be dedicated to data processing or perform other tasks which are quite general and not dedicated to the OCT device. The processor 121 may contain for example a field-programmable gate array (FPGA), a digital signal processor (DSP), an application specific integrated circuit (ASIC), a graphics processing unit (GPU), a system on chip (SoC) or a combination thereof, that performs some, or the entire data processing steps, prior to passing on to the host processor or in a parallelized fashion.

The interference causes the intensity of the interfered light to vary across the spectrum. The Fourier transform of the interference light reveals the profile of scattering intensities at different path lengths, and therefore scattering as a function of depth (z-direction) in the sample. The profile of scattering as a function of depth is called an axial scan (A-scan). A set of A-scans measured at neighboring locations in the sample produces a cross-sectional image (tomogram or B-scan) of the sample. A collection of B-scans collected at different transverse locations on the sample makes up a data volume or cube. For a particular volume of data, the term fast axis refers to the scan direction along a single B-scan whereas slow axis refers to the axis along which multiple B-scans are collected. A variety of ways to create B-scans are known to those skilled in the art including but not limited to along the horizontal or x-direction, along the vertical or y-direction, along the diagonal of x and y, or in a circular or spiral pattern.

The sample and reference arms in the interferometer could consist of bulk-optics, fiber-optics or hybrid bulk-optic systems and could have different architectures such as Michelson, Mach-Zehnder or common-path based designs as would be known by those skilled in the art. Light beam as used herein should be interpreted as any carefully directed light path. Instead of mechanically scanning the beam, a field of light can illuminate a one or two-dimensional area of the retina to generate the OCT data (see for example, U.S. Pat. No. 9,332,902; D. Hillmann et al, "Holoscopy—holographic optical coherence tomography" *Optics Letters* 36(13): 2390 2011; Y Nakamura, et al, "High-Speed three dimensional human retinal imaging by line field spectral domain optical coherence tomography" *Optics Express* 15(12):7103 2007; Blazkiewicz et al, "Signal-to-noise ratio study of full-field Fourier-domain optical coherence tomography" *Applied Optics* 44(36):7722 (2005)). In time-domain systems, the reference arm needs to have a tunable optical delay to generate interference. Balanced detection systems are typically used in TD-OCT and SS-OCT systems, while spectrometers are used at the detection port for SD-OCT systems. The invention described herein could be applied to any type of OCT system. The OCT system could be a stand-alone diagnostic instrument or be integrated within a surgical microscope such as the ZEISS OPMI LUMERA® with RESCAN™.

In FIG. 1, lens (123) is normally called the objective or ocular lens. It is present to produce a focused beam onto a desired part of the eye. In order to accommodate anterior segment (cornea, aqueous humor, and crystalline lens) and posterior segment (vitreous humor and the various retinal tissues down to the sclera), the lens (123) needs to have its focal length adjusted. There are a variety of ways to achieve this, but often a method is to insert or add a negative lens at a position just downstream of its rear vertex (124). Such a lens could be added manually by the user and attached to the system via magnets or any other attachment mechanism known to one skilled in the art. Thus, in this particular approach, addition of this lens to the optical configuration of the system permits the instrument to switch between anterior and posterior imaging.

Commercial OCT devices have been developed in the past for imaging both the anterior and posterior sections of the eye. Some of these are, for example, Zeiss Cirrus™ HD-OCT, Visante™ Omni, and Stratus™ (Carl Zeiss Meditec, Inc. Dublin, Calif.)). The Cirrus™ HD-OCT system allows for imaging both the anterior and posterior regions by inserting a lens to change the focal properties of the system and adjusting the delay line between the sample and reference arms as described in US Publication No. 2007/0291277. The Cirrus™ HD-OCT produces images of the anterior segment of an eye by using spectral domain optical coherence tomography (SD-OCT) technology.

Motion-Correction in Corneal Scans

Figure 2A:
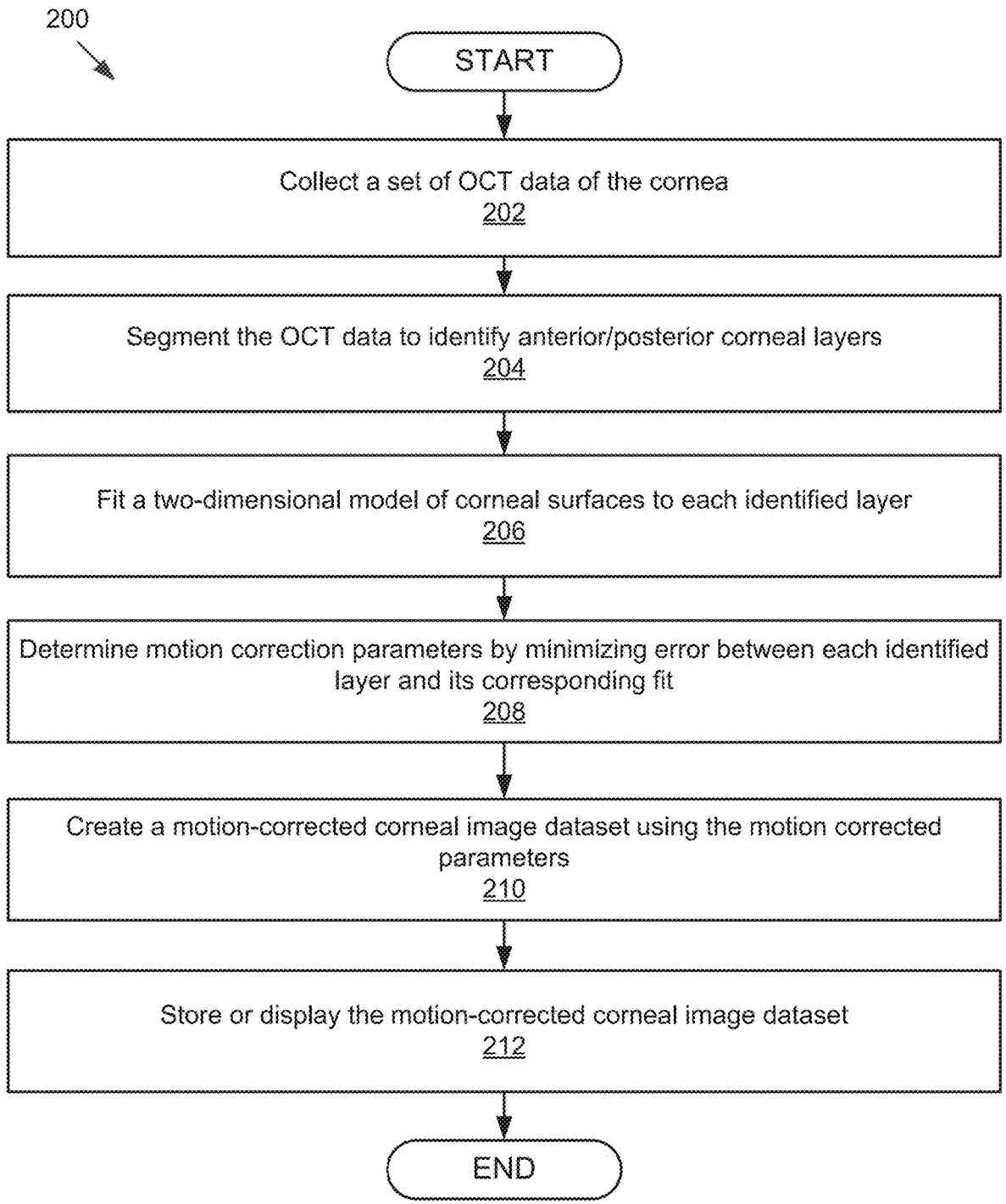
FIG. 2A is a flowchart of an example method for correcting the effects of eye motion that may occur during data acquisition of a cornea of an eye.

FIG. 2A shows a method 200 for correcting the effects of eye motion that may occur during data acquisition of a cornea of an eye. It should be understood that the method 200 described herein is not limited to the steps and/or operations referenced in this method and that other steps and/or operations are also possible and are within the scope of the present disclosure. It should also be understood that not every step described herein must be performed.

In block 202, a set of OCT data of the cornea of an eye is collected. The OCT data may comprise a plurality of B-scans acquired over a series of transverse locations on the cornea. These B-scans could be of any number or shape of scans (e.g., meridional or radial, circular, spiral, etc.). In a preferred embodiment, these B-scans can consist of N sets of perpendicular meridional B-scans or a cube scan. In some embodiments, the scans are collected with a longer scan time (e.g. denser scans or repeated B-scans at the same location, which could take anywhere between 50 ms and few seconds) and thus are likely affected by the effects of eye motion including one or both of axial and transverse eye motion.

In block 204, the OCT data (i.e., the B-scans) are segmented to identify anterior or posterior corneal layers. One effective way of segmenting the B-scans takes advantage of the fact that the general shape of the cornea can be modeled as a quadric surface. In this approach, initial estimates of the anterior and posterior layers are first identified. To estimate the initial position of anterior and posterior surface, a normalized cross-correlation is performed between each A-scan and two functions. The first function represents the approximate transition from air to stroma and the second function represents the approximate transition from stroma to aqueous humor. The positions with the highest normalized cross-correlation values are recorded as the initial estimate of the anterior or posterior surface. A corneal layer in a two-dimensional B-scan can be assumed to be a conic section (parabola, ellipse, hyperbola, etc.). A parabola is fitted to the initial estimated values using a robust regression method such as random sample consensus (RANSAC) by robustly estimating the parameters of parabola from the data which contains outliers. The final estimates of the layer position can then be found using a hybrid graph theory and dynamic programming framework (see for example, S. Timp et al. (2004). "A new 2D segmentation method based on dynamic programming applied to computer aided detection in mammography." Medical Physics 31(5): 958-971). In this framework, the parabola fitted to the initial estimated values is used to define a region of interest (ROI) as the region around this parabola. After an ROI containing a layer (anterior or posterior) is identified, the graph-based segmentation can be performed within the ROI to obtain the anterior/posterior layer. It should be understood, the segmentation is not limited to graph-based segmentation and other segmentation approaches are also possible and are within the scope of the present disclosure.

In block 206, a two-dimensional model of the corneal surfaces is then fitted to the corneal layers identified in block 204. In a preferred embodiment, the surface model can be a quadric (e.g., rotated/tilted paraboloid, ellipsoid, hyperboloid, sphere, etc.) or a Zernike polynomial, generally of a lower order. The lower order ensures that the motion correction is possible even in the presence of segmentation error(s) due to noise and pathology. One method by which the model may be fitted is a robust fitting method, such as RANSAC fitting. This forms the initial estimate of the corneal surface. RANSAC assumes that the data contains data points that are gross errors or outliers, in addition to other data points that are inliers and whose distribution can be explained by some set of model parameters. As such, it is able to smooth data sets in which outliers make up a significant portion of the data set. If a traditional technique for fitting a model, such as least squares, was used instead of the robust fitting method, these outlier data points could lead to inaccurate calculations of lower order of corneal surface.

The outliers can be due to, for example, extreme noise, erroneous measurements, or incorrect interpretation of the data. In the case of corneal imaging, the outliers can also be due to causes such as specular reflection, scarring or pathologies, curvature change after refractive surgery, blinking during data acquisition, interferences from eyelashes or eyelids, or other artifacts. By using RANSAC, these outliers can be detected and excluded from the model fit at each iteration.

Next, in block 208, motion correction parameters are determined by minimizing the error between each identified layer and the two-dimensional model of the corneal surfaces. In some embodiments, transformations (related to identified corneal layers) that minimize an objective function (see below) are selected as the motion correction parameters. The objective function can be a norm of the difference between the transformed surface points and the model fit. A possible additional term for an objective function could be filter operators (e.g., difference operators) to enforce smoothness since the underlying corneal surface is believed to be mostly continuous. One example way of minimizing the error or the objective function is given as follows:

$$X = [x_1, x_2, x_3, \ldots, x_N]^T \quad x_i = [x_i, y_i, z_i]^T$$

$$\min_T \|TX - q(TX)\|^2$$

$$lb \leq T \leq ub$$

where X contains the anterior corneal segmentation points after dewarping, T is the transformation matrix containing the transformation matrices for each point, q(.) represents the quadric or a Zernike fit (lower order) to the transformed points at each iteration of the minimization. The transformation parameters can be constrained using a lower bound (lb) and an upper bound (up) for each or a group of points (e.g. each meridian).

In some embodiments, the above minimization problem is solved by L-BFGS solver, which solves smooth, twice differentiable bounded non-linear programs using a limited memory BFGS Hessian update (see for example, C. Zhu, R. H. Byrd and J. Nocedal, "L-BFGS-B: Algorithm 778: L-BFGS-B FORTRAN Routines for Large Scale Bound Constrained Optimization," ACM Transactions on Mathematical Software 23(4), pp. 550-560, 2007).

In some embodiments, the most basic motion parameters are the x,y,z translation for each meridian scan. However, shear or tilt in each meridian scan can be incorporated into the transformation matrix for each meridian.

Figure 9:
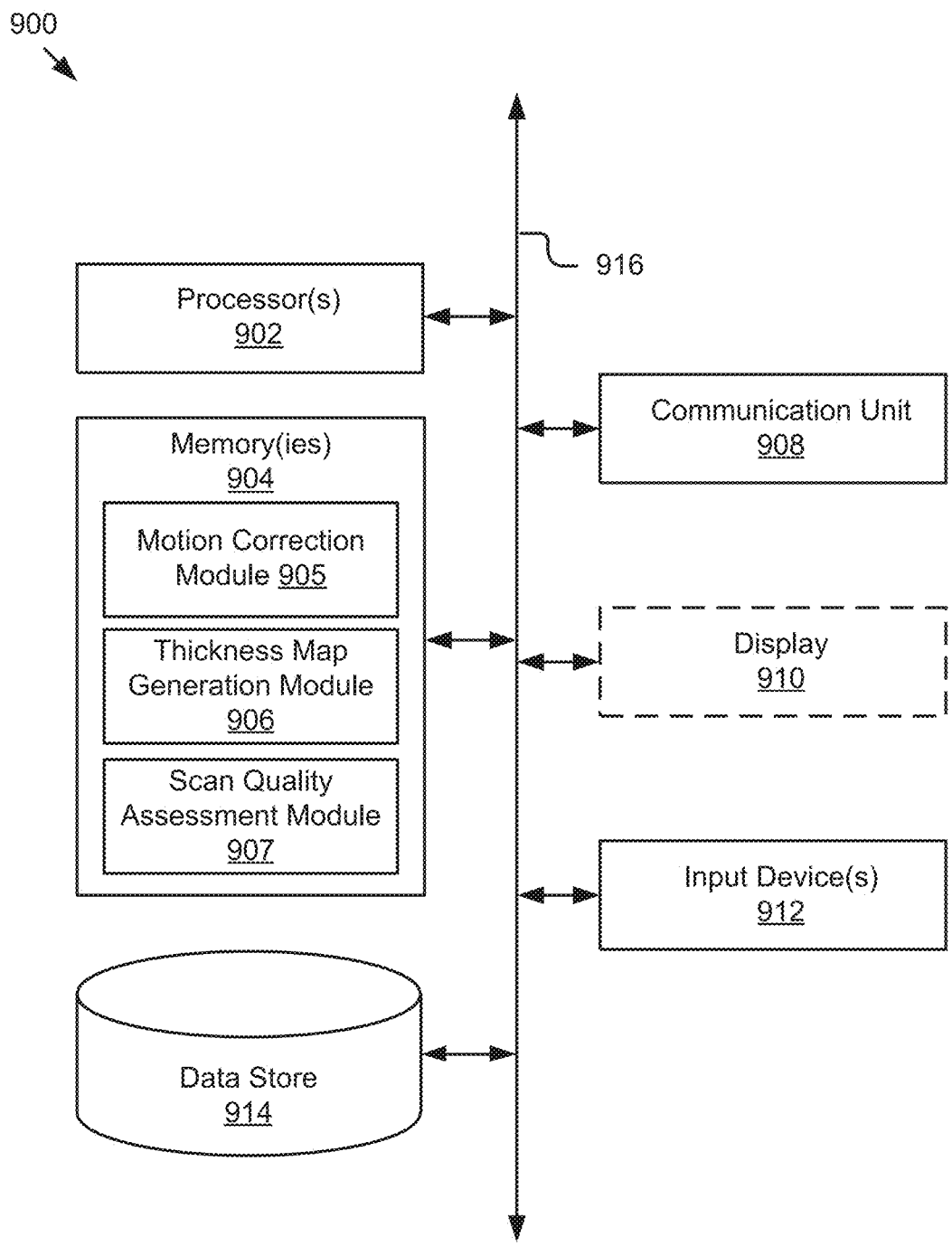
FIG. 9 is a block diagram of an example computer system configured to perform the functions discussed in the present application.

In block 210, a motion-corrected corneal image dataset is created using the motion correction parameters obtained in block 208, and then in block 212, the motion-corrected corneal image dataset is stored (e.g., in data store 914 shown in FIG. 9) or displayed (e.g., via display 122 or optional display 910 shown in FIG. 9). In some instances, the motion-corrected dataset is created from the original set of OCT data (collected in block 202) by correcting the lateral and z-displacement eye motion artifacts using the motion correction parameters. The motion-corrected corneal image dataset can then be used to create a motion-corrected model of the anterior and/or posterior surfaces of the cornea. Modeling the corneal surface is essential for certain anterior segment applications. One way of modeling the corneal surface that is particularly helpful is the use of Zernike polynomials. This type of polynomial is good for representing the corneal shape and provides an accurate solution when the underlying surface is relatively smooth and motion free. For certain applications, such as keratometry, the $7^{th}$ order Zernike polynomial that gives 36 Zernike coefficients adequately approximates the corneal surface. In some cases, the coefficients may be determined using a robust fitting algorithm, such as Random Sample Consensus (RANSAC) fitting. Once a motion-corrected model of the cornea is created, the method 200 can be extended to use the model for additional applications. These include obtaining highly accurate and dense pachymetry and epithelial thickness maps with minimal motion artifacts, keratometric values, and corneal power measurements.

Figure 3:
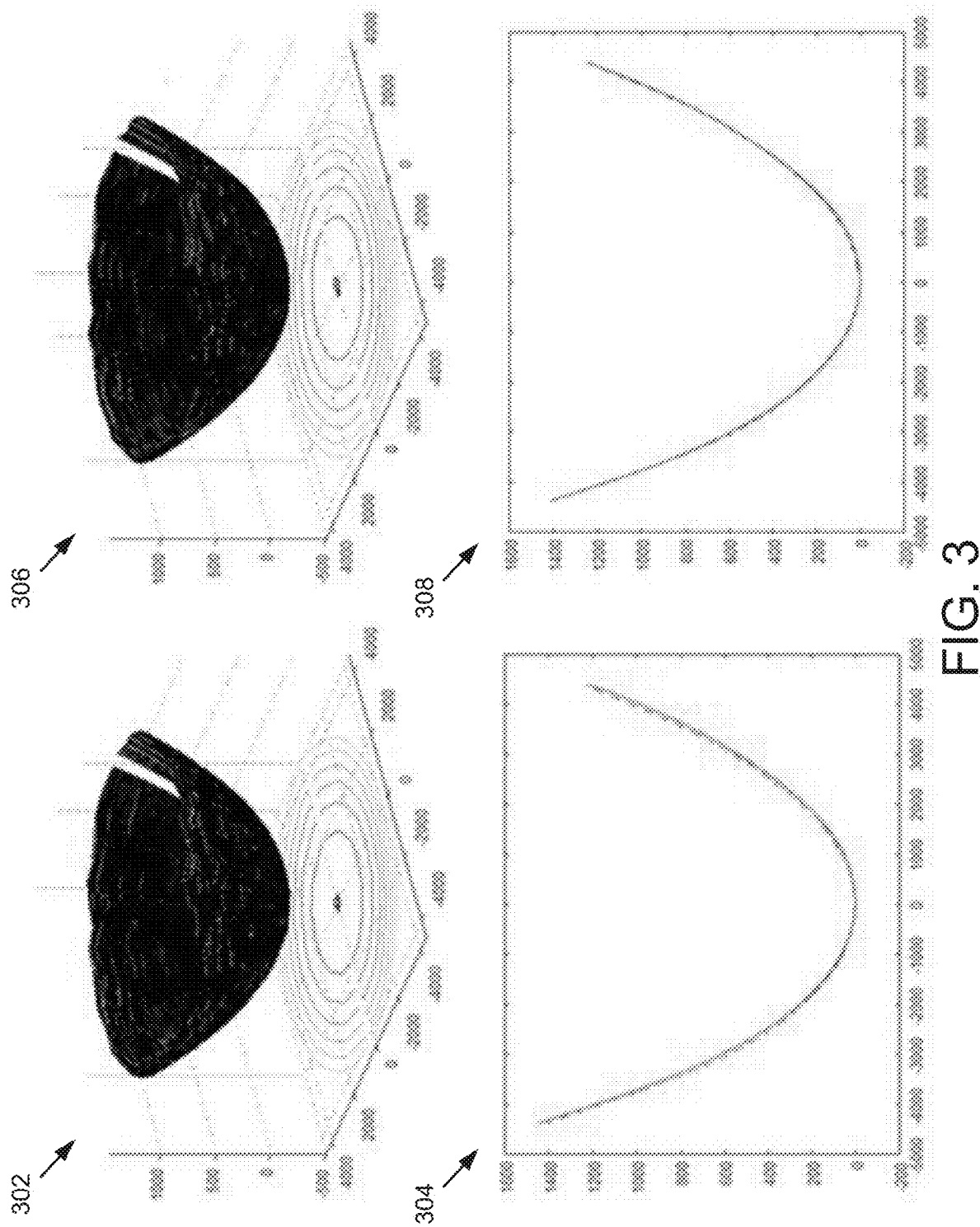
FIG. 3 shows an example of a projection of corneal surface contour lines onto the xy plane and a plot of a meridian and corresponding Zernike fit before and after the motion correction.
Figure 4:
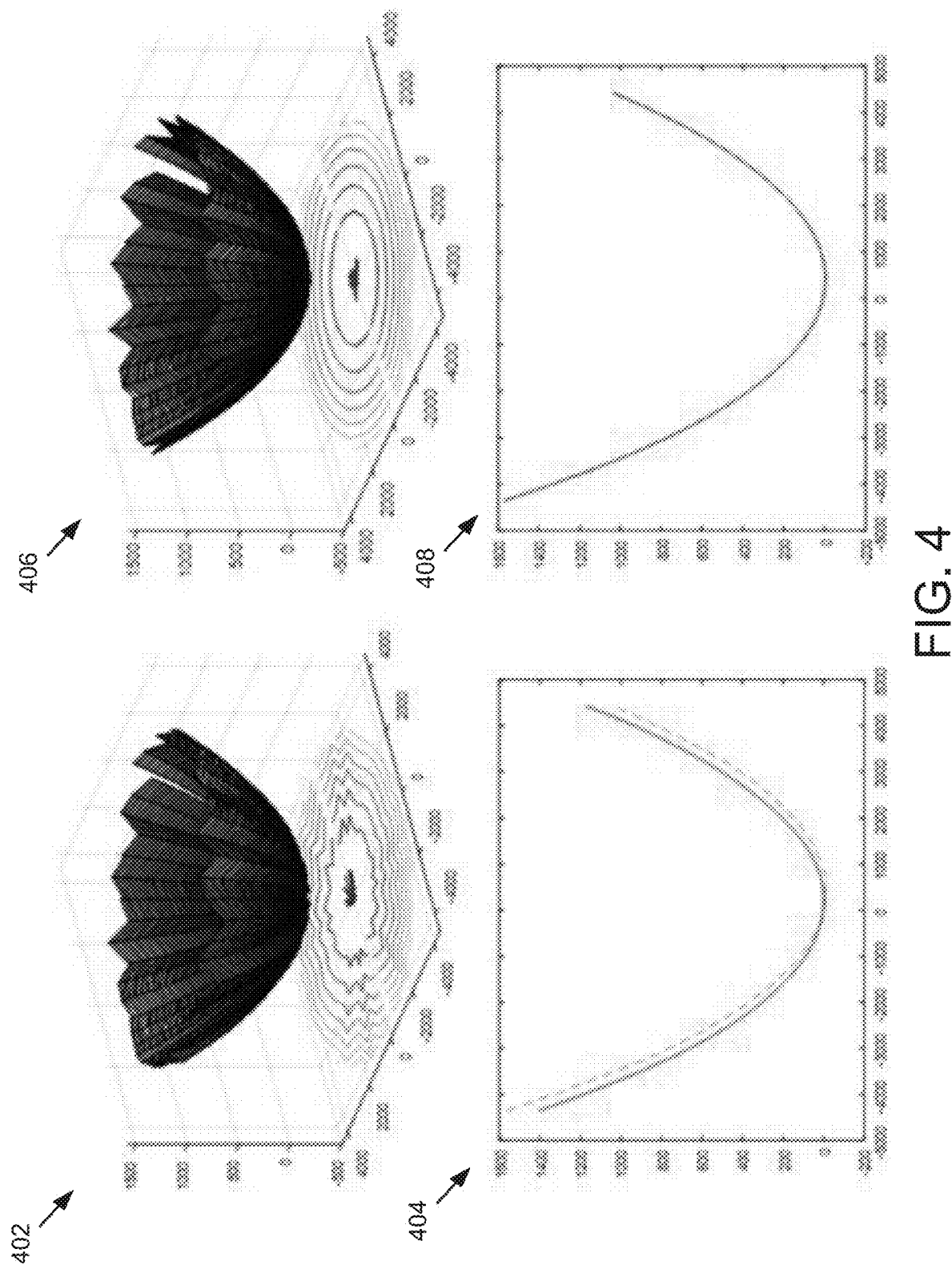
FIG. 4 shows another example of a projection of corneal surface contour lines onto the xy plane and a plot of a meridian and corresponding Zernike fit before and after the motion correction.

In some embodiments, the performance of the corneal motion correction method discussed above can be evaluated by calculating the root mean square (RMS) error between the anterior segmentation data and its $7^{th}$ order Zernike fit before and after motion correction. FIGS. 3 and 4 show exemplary plots of the projection of corneal surface contour lines (only data are plotted with no interpolation) onto the xy plane before and after motion correction (left and right plots, respectively). In particular, FIG. 3 shows, for a scan with small motion, the projection of the corneal surface contour lines onto the xy plane 302 and the plot of a meridian and corresponding Zernike fit 304 before the motion correction, and the projection of the corneal surface contour lines onto the xy plane 306 and the plot of the same meridian and corresponding Zernike fit 308 after the motion correction. As depicted, the projection of contour lines show circular/elliptical shapes after motion correction. The data (blue dashed lines) and the fit (red line) for a given meridian are shown in the plots 304 and 308. In this particular example of FIG. 3, the RMS error is 9.16 microns before the motion correction and 4.75 microns after the motion correction.

FIG. 4 shows, for a scan with large motion, the projection of the corneal surface contour lines onto the xy plane 402 and the plot of a meridian and corresponding Zernike fit 404 before the motion correction, and the projection of the corneal surface contour lines onto the xy plane 406 and the plot of the same meridian and corresponding Zernike fit 408 after the motion correction. Here, the RMS error is 48.14 microns before the motion correction and 5.66 microns after the motion correction.

Scan Quality Assessment in Corneal Image Data

Figure 2B:
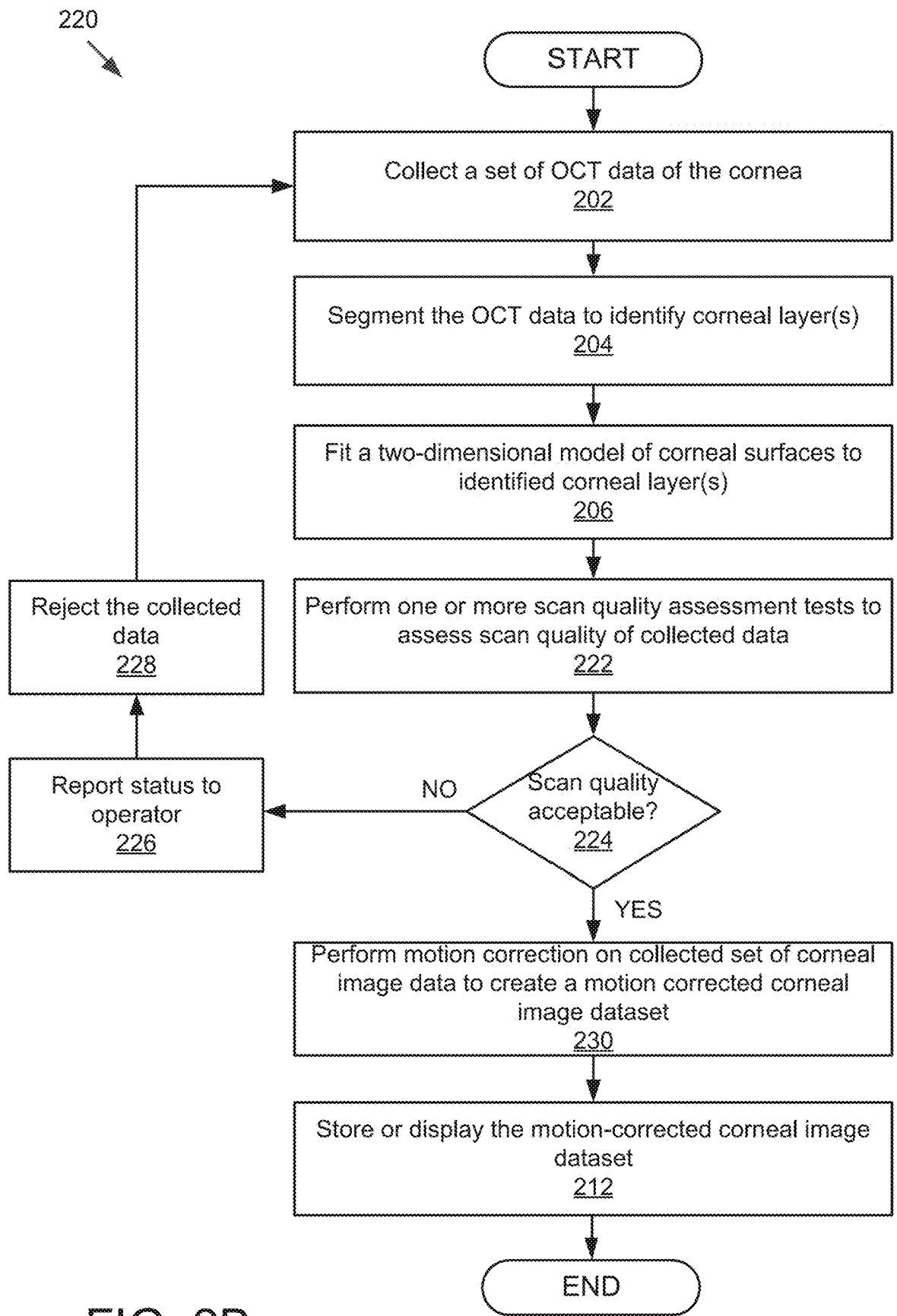
FIG. 2B is a flowchart of an example method for assessing scan quality of corneal image data collected using an OCT system.

FIG. 2B shows a method 220 for assessing scan quality of corneal image data collected using an OCT system. It should be understood that the method 220 described herein is not limited to the steps and/or operations referenced in this method and that other steps and/or operations are also possible and are within the scope of the present disclosure. It should also be understood that same reference numerals are used to refer to the steps discussed above with respect to FIG. 2A, the description for which will not be repeated here.

In step 202, a set of OCT data of the cornea of an eye is collected. The OCT data as discussed elsewhere herein may comprise a plurality of B-scans acquired over a series of transverse locations on the cornea. In a preferred embodiment, these B-scans can consist of N sets of perpendicular radial B-scans or a cube scan. In some embodiments, the scans are collected with a longer scan time (e.g. denser scans or repeated B-scans at the same location, which could take anywhere between 50 ms and few seconds) and thus are likely affected by eye motion including one or both of axial and transverse eye motion.

In step 204, the OCT data (i.e., the B-scans) are segmented to identify one or more corneal layers based on a segmentation approach discussed above with respect to FIG. 2A. Next, in step 206, a two-dimensional model of the corneal surfaces is fitted to the one or more corneal layers. In a preferred embodiment, the surface model can be a quadric (e.g., rotated/tilted paraboloid, ellipsoid, hyperboloid, sphere, etc.) or a Zernike polynomial, generally of a lower order. One method by which the model may be fitted is a robust fitting method, such as RANSAC fitting.

In step 222, one or more scan quality assessment tests are performed to assess scan quality of the collected data based on the results of the segmentation (step 204) and fitting (step 206). The one or more scan quality assessment tests may include, for example and without limitation, 1) a scan quality test based on confidence values in the results of the segmentation (steps 252-256 in FIG. 2C), 2) a scan position test based on z-position of the vertex of each B-scan in the OCT data (steps 258-266 in FIG. 2C), 3) a vertex off center finding test based on the distance between the vertex position and center of a B-scan (steps 268-272 in FIG. 2D), and 4) a motion test based on a root mean square (RMS) error between the one or more corneal layers and the two-dimensional model of the corneal surfaces (steps 274-278), each of these tests is discussed in further detail below with respect to FIGS. 2C and 2D.

In step 224, a determination is made as to whether the one or more scan quality assessment tests meet an acceptable scan quality condition. For instance, one of the scan quality assessment tests may include computing an error between the one or more corneal layers and the two-dimensional model of the corneal surfaces (e.g., $7^{th}$ order Zernike polynomial) and then determining whether the error is below a certain threshold (e.g., 60 micron) in order to meet an acceptable scan quality condition. The error between a corneal layer or surface and the two-dimensional model may be large due to 1) blink or partial blink in scan data, 2) low contrast at the corneal surfaces, 3) large lateral and axial eye motion, 4) low or high scan position, 5) off-centered scans, etc. In some instances, the error can be computed using an error metric such as, for example, root mean squared error (RMSE), the sum of square due to error (SSE), R-sqaure, and/or adjusted R-sqaure.

If a scan quality condition is determined to be not satisfied or acceptable in step 224, then its status can be reported to an operator (step 226), discussed in more detail below with respect to FIGS. 2C and 2D. An example status may include one or more of a 1) poor scan quality (due to blink, eyelid/eyelash interference, low contrast, etc.), 2) large motion (e.g., lateral, rotational motion and tilt in scans), 3) scan position too high, 4) scan position too low, 5) vertex off center, etc. In response to the indication that the condition is not met, the current collected OCT data may be rejected (step 228) and the method 220 may return to automatically collect a new set of corneal image data (step 202) and perform subsequent operations thereon.

If on the other hand, the condition is determined to be satisfied, then, in step 230, motion correction is performed on the collected set of corneal image data to create a motion corrected corneal image dataset. In some embodiments, the motion correction step involves determining motion correction parameters by minimizing error between the one or more corneal layers and the two-dimensional model of the corneal surfaces (step 208 of FIG. 2A) and then creating a motion corrected corneal image dataset using the motion corrected parameters (step 210 of FIG. 2A). The motion-corrected corneal image dataset may then be stored (e.g., in data store 914 shown in FIG. 9) or displayed (e.g., via display 122 or optional display 910 shown in FIG. 9) as discussed elsewhere herein.

Figure 2C:
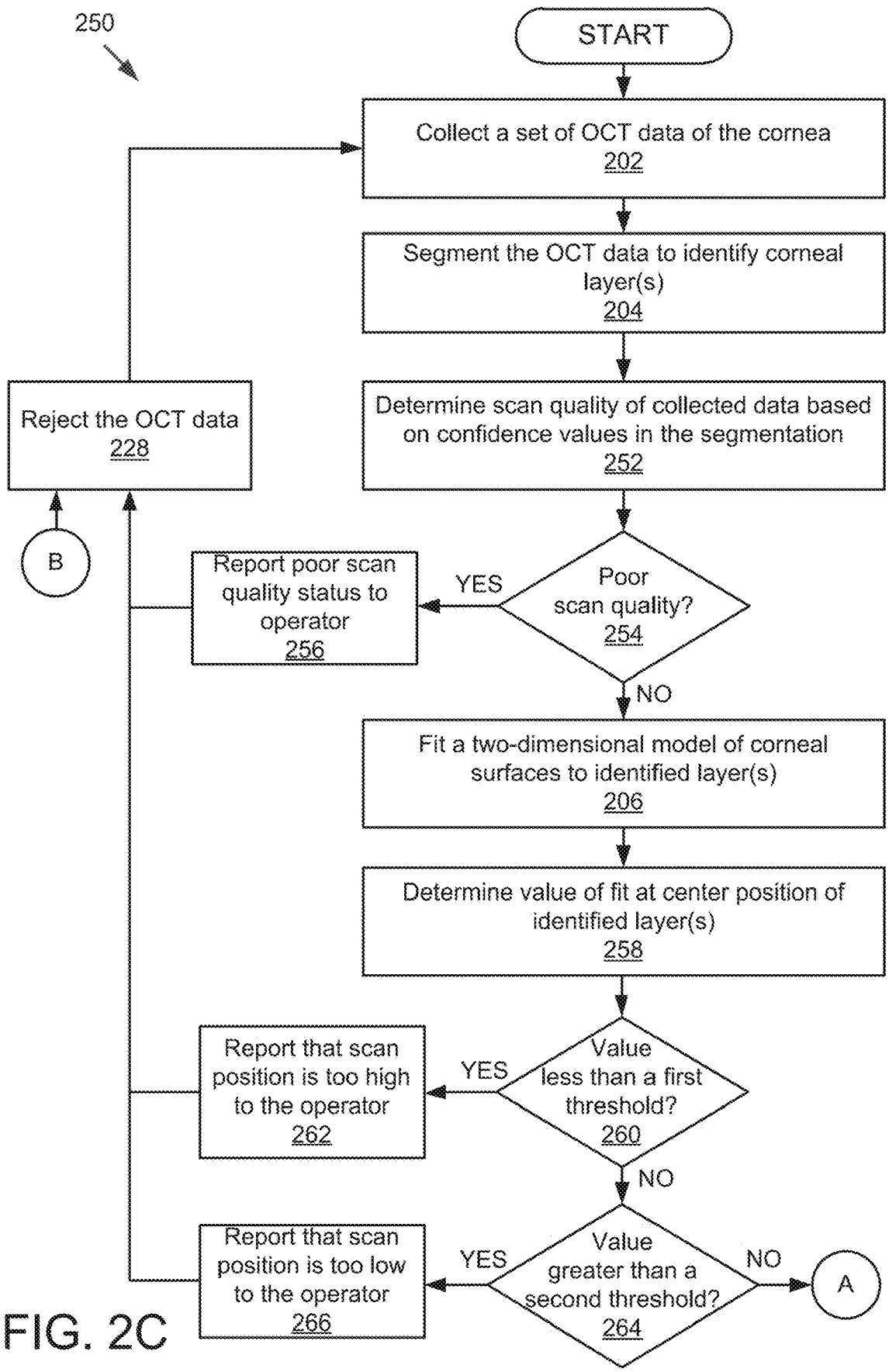
FIGS. 2C and 2D are flowcharts of a more specific method of scan quality assessment.
Figure 2D:
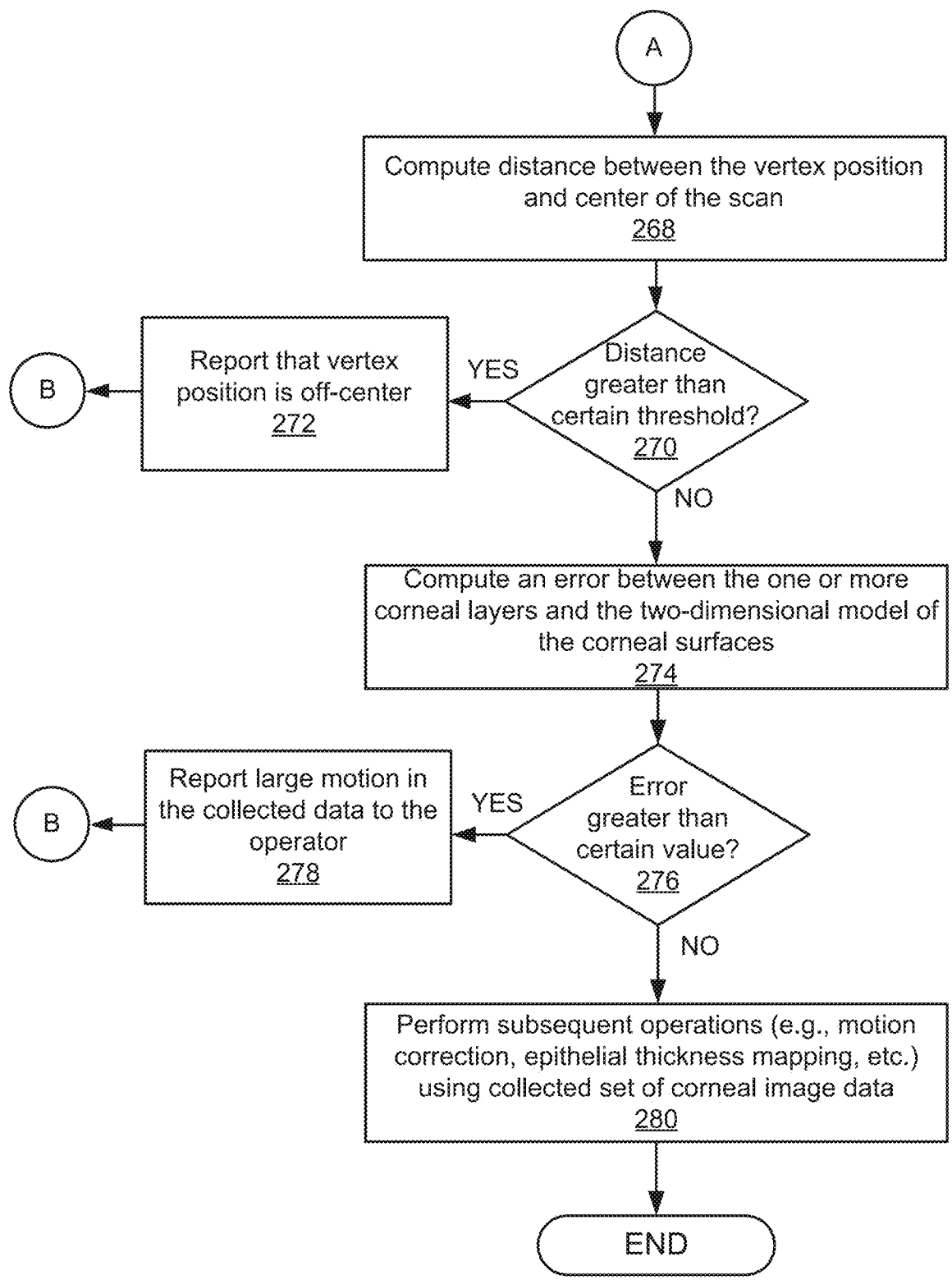

FIGS. 2C and 2D show a more specific method 250 of scan quality assessment. In particular, the method 250 describes a series of scan quality assessment tests or metrics that may be performed to assess the quality of corneal image data at various steps and to report an operator about the status on each metric. It should be understood that the method 250 is not limited to the scan quality assessments tests/metrics referenced in this method and that other tests/metrics are also possible and are within the scope of the present disclosure. Also, it should be understood that the same reference numerals are used to refer to the steps discussed above with respect to FIGS. 2A and 2B, the description for which will not be repeated here.

After the one or more anterior or posterior corneal layers are identified by segmenting the OCT data (step 204 of FIGS. 2A and/or 2B), scan quality of the collected data is determined based on confidence values in the results of the segmentation (step 252). The confidence values may range from −1 to 1 where −1 indicates a low confidence in the segmentation and 1 indicates a high confidence in the segmentation. If any anterior corneal layer has a low confidence value for a given length (e.g., 1000 micron) in any of its peripheral regions, then the scan is considered to have a poor quality. As discussed elsewhere herein, the poor scan quality may be caused by blink, partial blink, eyelid/eyelash interference, and low contrast, which affects the confidence on the segmentation specifically in the peripheral regions.

In step 254, if the scan quality is determined to be of poor quality, then a poor scan quality status is reported to an operator (step 256). Otherwise, the method 250 proceeds to step 206 to fit a two-dimensional model of the corneal surfaces to the one or more corneal layers identified in step 204. For instance, a polynomial second order ($y=a_1x^2+a_2x+a_3$) is fitted to the 3000 micron central region of each anterior layer or surface using RANSAC robust fit. The center position of the anterior surface is the origin. In step 258, a value of the fit is determined at the center position of the one or more identified layers and then a decision is made as to whether the value is less than a first threshold (step 260) or more than a second threshold (step 264). The first and the second thresholds are different. If the value of the fit at the center position of any anterior layers of B-scans is less than a first threshold (e.g. 50 micron), then the scan is considered to be too high and a "scan too high" status is reported to the operator (step 262). Otherwise, if the value of the fit at the center position of any anterior layers of B-scans is greater than a second threshold (e.g. 500 micron), then the scan is considered to be too low and a "scan too low" status is reported to the operator (step 266). The scan being too low or too high may be caused by axial motion during scan or by misalignment.

Figure 2E:
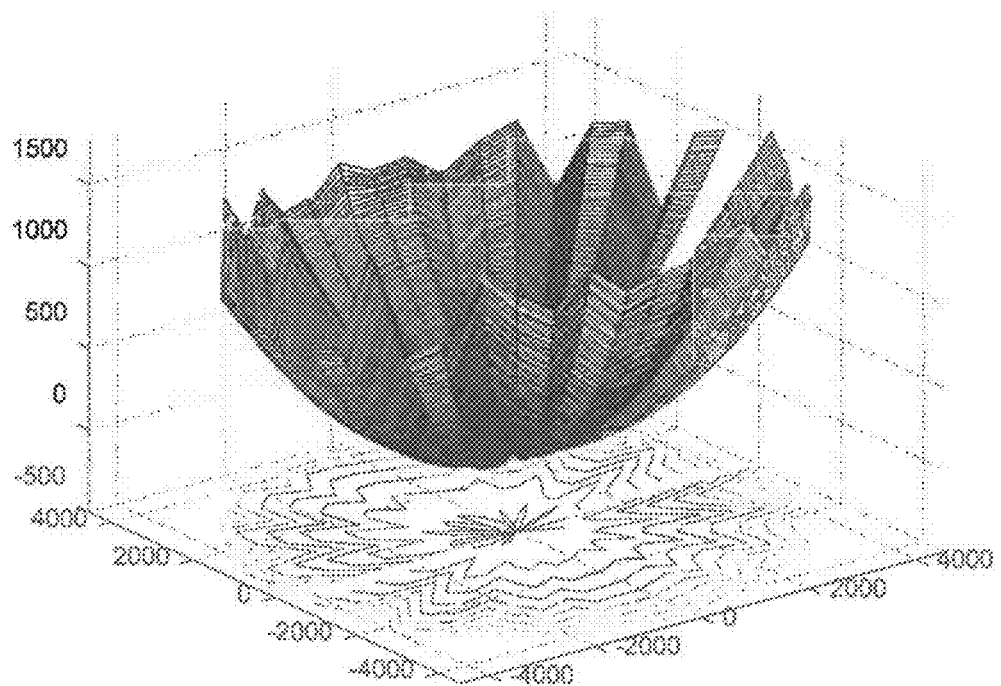
FIGS. 2E and 2F shows two exemplary anterior segmentation plots each with a root mean square error (RMSE) beyond a certain threshold indicating large motion in scan data.
Figure 2F:
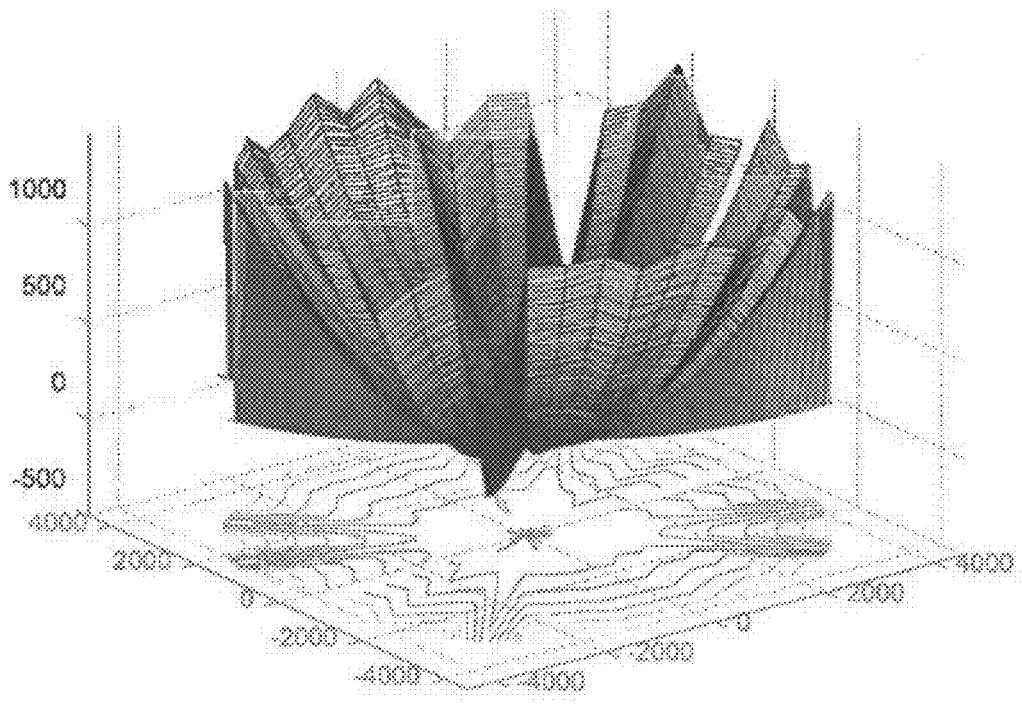

The method 250 then proceeds to step 268 (FIG. 2D) to compute a distance between the vertex position and the center or a predefined position of the scan. If the distance is greater than a certain threshold (e.g., 500 micron) in step 270, then the vertex position is considered to be off center and its status is reported to the operator (step 272). Next, in step 274, an error is computed between the one or more corneal layers and the two-dimensional model of the corneal surfaces. For instance, RMS error (RMSE) between the anterior segmentation and its $7^{th}$ order Zernike polynomial can be computed to determine amount of motion in the collected data or scans. If the error is greater than a certain value (e.g., 60 micron) (step 276), then the collected data contains large motion and cannot be used as an input to the corneal motion correction algorithm (e.g., the motion correction module 905 in FIG. 9). By way of example illustrations, FIG. 2E shows an anterior segmentation plot with a RMSE of 115 microns indicating large motion. FIG. 2F shows another anterior segmentation with a RMSE of 149 microns indicating large motion and blink in the scan data.

In step 278, a status indicating large motion in the collected data is reported to the operator. In response to the status reported to the operator in steps 256, 262, 266, 272, and/or 278, the collected OCT data may be rejected (step 228 in FIG. 2C) and the method 250 may return to collect a new set of corneal image data (step 202) and perform subsequent operations thereon.

If the result of the decision in step 276 is also negative like the previous steps 254, 260, 264, and 270, then the collected corneal image data is considered to be good and of meeting the desired quality standards or metrics. In step 280, the corneal image data can then be used as an input to various algorithms such as the motion correction module 905 (FIG. 9) to perform motion correction (discussed in reference to FIG. 2A) and/or the thickness map generation module 906 (FIG. 9) to perform epithelial thickness mapping (discussed in reference to FIG. 6).

Epithelial Thickness Maps

Figure 5:
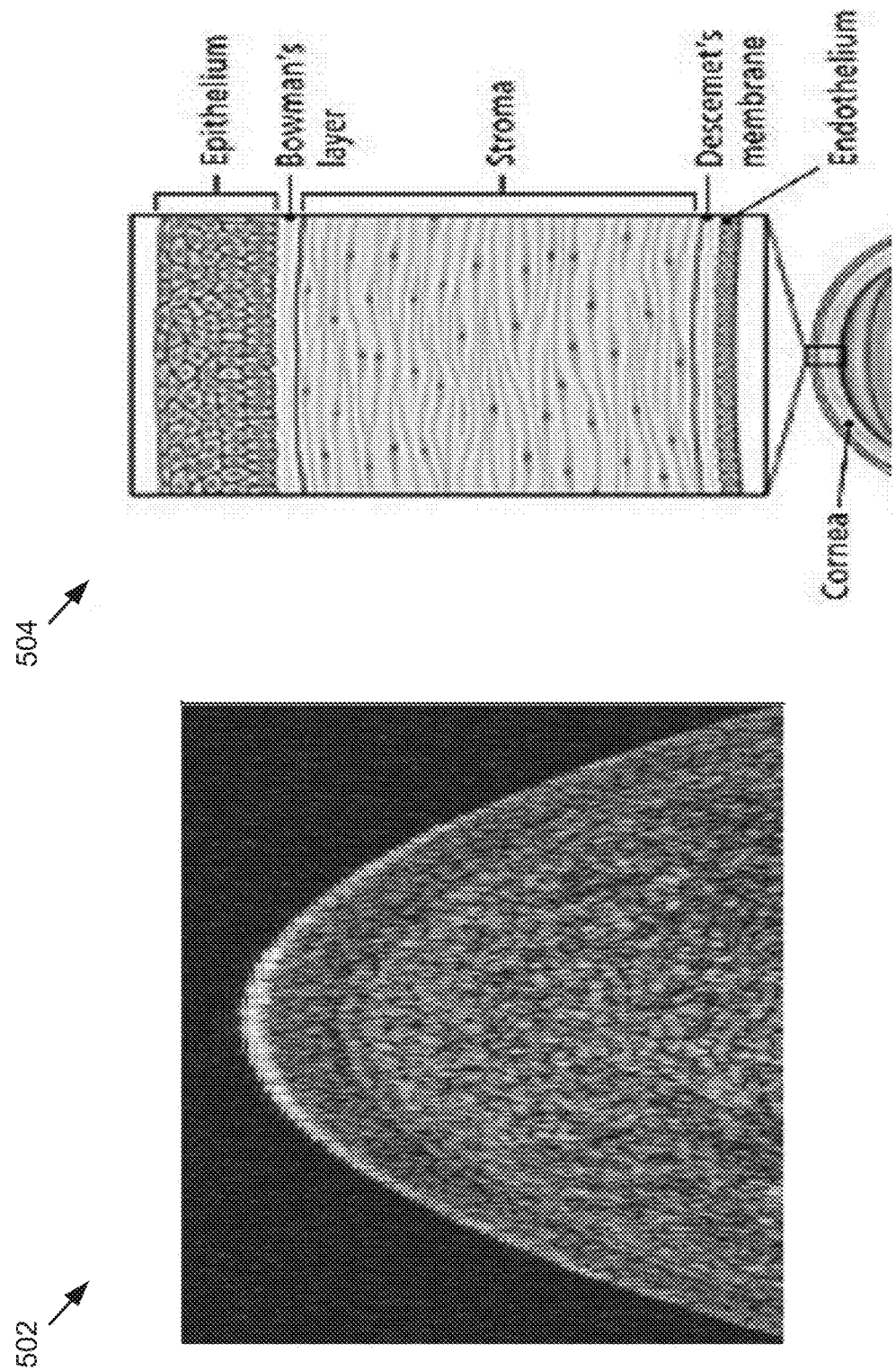
FIG. 5 shows a SD-OCT central corneal B-scan and a detailed vertical section view of human cornea.

In another aspect of the present application, a two-dimensional epithelial thickness map can be created based on, for example, a radial scan pattern used in the central cornea scan. FIG. 5 shows a SD-OCT central corneal B-scan 502 and a detailed vertical section view 504 of human cornea. The thickness map is created based on the anterior and the outer boundary of Bowman's layers. For each radial B-scan, the thickness is defined as the closest distance from the anterior to the outer boundary of Bowman's layer. Similar to a pachymetry map, the epithelial thickness map is interpolated from polar coordinates into a two-dimensional Cartesian map.

The invention discussed herein solves a challenging Bowman's layer segmentation problem in the art due to following facts in OCT images:

Using a single B-scan (not averaged B-scan from multiple B-scans from the same location)

Very narrow intensity difference between corneal epithelium and stroma.

Disconnected Bowman's layer seen within a B-scan.

Anterior surface of the stroma is located a few microns below the Bowman's layer and can be confused with the Bowman's layer.

Weak signal at Bowman's layer seen in the peripheral regions.

Figure 6:
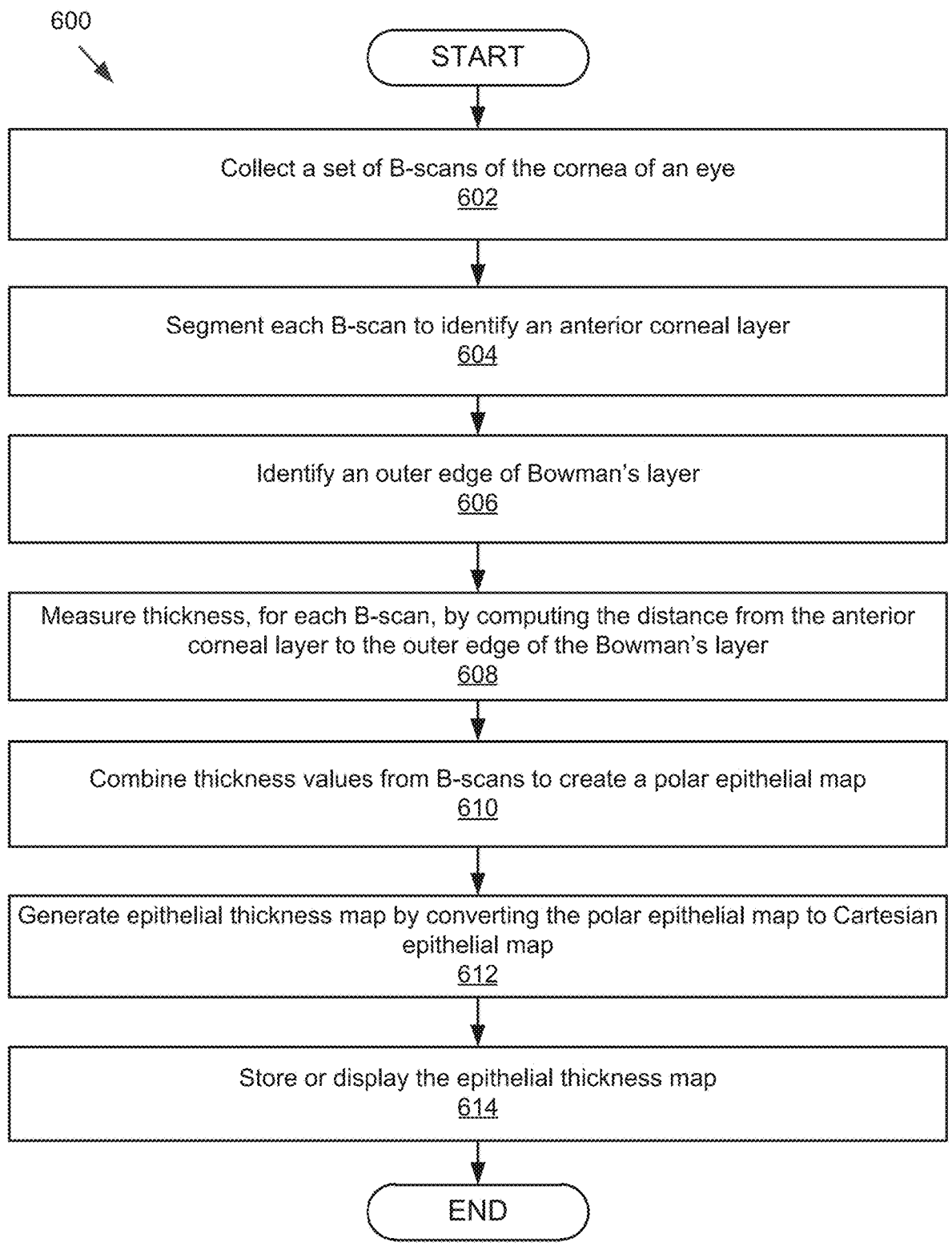
FIG. 6 is a flowchart of an example method for generating an epithelial thickness map.

FIG. 6 shows a method 600 for generating an epithelial thickness map according to the present application. It should be understood that the method 600 described herein is not limited to the steps and/or operations referenced in this method and that other steps and/or operations are also possible and are within the scope of the present disclosure.

The method 600 begins by collecting, in block 602, a set of B-scans of the cornea of an eye. In some embodiments, the B-scans are collected over a range of different transverse locations on the cornea such that no two B-scans are collected at the same transverse location. In some instances, a B-scan may be optionally downsampled by a factor of 2 in the lateral direction to produce a smaller B-scan to estimate a region of interest (ROI). Downsampling reduces the overall execution time. Next, in block 604, each B-scan is segmented to identify an anterior corneal layer. The segmentation can be carried out in the same way using a dynamic programming framework as discussed above with respect to block 204 of method 200. The B-scan may be flattened to the anterior layer in a search region of 100 microns. Optionally, average filtering may be performed in the lateral direction to increase the signal to noise ratio (SNR) and axial gradient to enhance the Bowman's layer edges.

In block 606, an outer edge of the Bowman's layer is identified. After the ROI containing surface of interest (i.e., area around the Bowman's layer) is identified in block 604, segmentation can be performed within the ROI. For example, graph based segmentation can be performed.

This segmentation works well on a total cost function c. The local cost functions are derived, for instance, from the image gradient magnitude in A-scan direction. Local cost is the cost assigned to every single pixel in the ROI. The pixels that most likely belong to the surface will be assigned low cost and vice versa (see for example, S. Timp, "A new 2D segmentation method based on dynamic programming applied to computer aided detection in mammography," Med. Phys. 31(5): 958-71 (2004)). In one embodiment, the total cost function c can be computed as follows:

$$c = \frac{1}{1+e^{\frac{((I*G_z)*G_x-\beta)}{\alpha}}}$$

where '*' stands for convolution.

I is the input image.

$G_z$ is the derivative of a Gaussian function with $\sigma_z$ in the axial direction.

$G_x$ is a Gaussian smoothing function with $\sigma_x$ in the lateral direction, and $\alpha$ and $\beta$ are sigmoid function parameters.

To find the path (or the edge positions) of the lowest cost when travelling in the image from left to the right, a cumulative cost function is constructed as below:

Set the first column of this cumulative cost function to the total (local) cost of these pixels:

$$C(i,0)=c(i,0)$$

The cumulative cost of the other pixels is calculated recursively:

$$C(i, j) = \min_{-m \leq k \leq m} \{C(i-k, j-1) + c(i, j)\}$$

where m is the search window in the previous column.

Once the cumulative cost function is established, the optimal path (or the surface) can be found by back-tracing the path from the last column to the first column for the lowest cumulative cost.

Figure 7B:
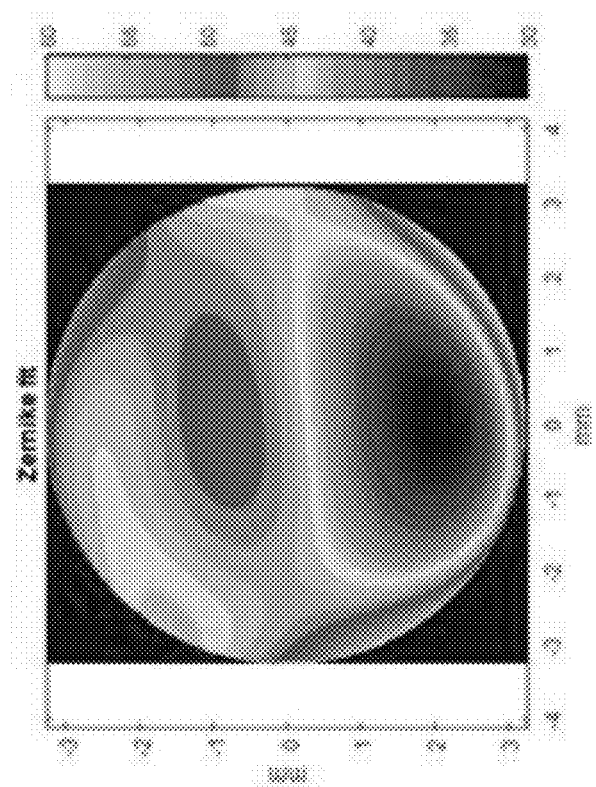
FIG. 7B shows an epithelial thickness map created based on a Zernike fitting.
Figure 7A:
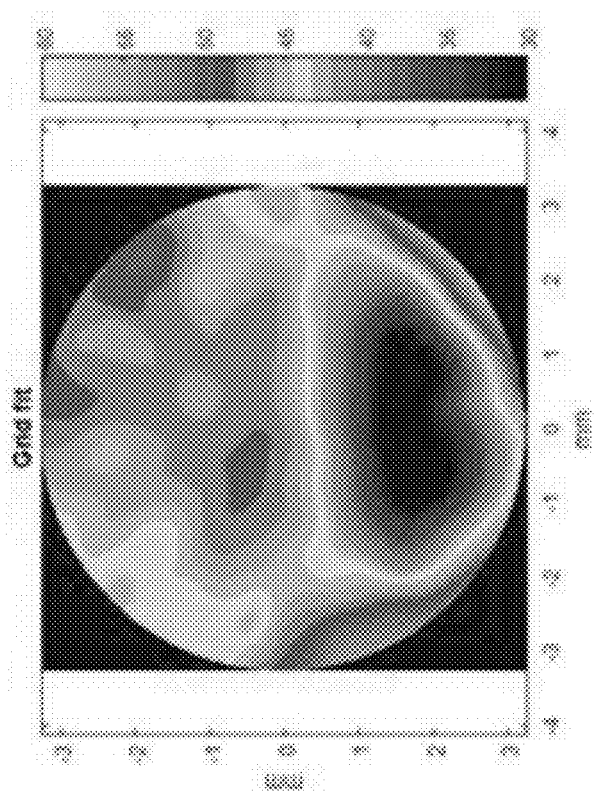
FIG. 7A shows an epithelial thickness map created based on a grid fit method.

Next, in block 608, the thickness is calculated for each B-scan individually. The thickness is measured as the distance from the anterior corneal layer to the outer edge of the Bowman's layer. In some embodiments, this distance is calculated using a distance transform method, such as a fast marching method (see for example, Telea, A. (2004). "An Image Inpainting Technique Based on the Fast Marching Method." Journal of Graphics Tools 9(1): 23-34 In block 610, the thickness values of all B-scans are combined to create a polar epithelial thickness map, which is then converted, in block 612, to a two-dimensional Cartesian map to obtain the epithelial thickness map. This conversion can be based on a grid fit method, Zernike fitting, or other interpolation methods. FIG. 7A shows the epithelial thickness map created based on the grid fit method. FIG. 7B shows the epithelial thickness map created based on the Zernike fitting. These two fitting methods are individually discussed below:

Grid Fit

Polar to Cartesian conversion is a fitting of the form z(x, y) to polar data. Grid fit can also fit a surface to scattered (or regular) data. The bilinear interpolation at any point inside the grid is a linear combination of the values at the grid nodes in the locality of the given point. The interpolation problem can be written as a regularization problem:

$$\min_z \|(Az - b)\|^2 + \lambda \|\beta_z\|^2$$

where the vector z is of length m×n; n is the number of grid nodes in they direction; m is the number of nodes in the x direction; A is a matrix of k×(m×n), where k is the number of data point; and b is a vector of known surface values. B is matrix of k×(m×n) containing the first partial derivatives of the surface in neighboring cells. $\lambda$ is the regularization parameter. If $0<\lambda<<1$, then the surface will be noisy. The surface will be smoother for $\lambda>1$. (see for example, John R. D'Errico, Understanding Gridfit, Dec. 28, 2006)

Zernike Fitting

Zernike polynomials model and represent the corneal shape. Zernike fitting provides an accurate solution when the underlying surface is relatively smooth and well-represented by a high order Zernike surface. Zernike fitting smooths the corneal data and provides a low pass filtering effect. The discrete set of data points in the polar coordinate system are expanded into Zernike polynomials such that $$z(\rho_i, \theta_i) = \sum_{n,\pm m} a_{n,\pm m} Z_n^{\pm m}(\rho_i, \theta_i)$$

for all points $(\rho_i, \theta_i)$. $Z_n^{\pm m}(\rho_i, \theta_i)$ are the Zernike polynomials.

To transform a polar map to Cartesian coordinates, a Zernike fit provides an accurate solution. The Zernike fitting could be applied to corneal surfaces (anterior and posterior) as well as to the corneal map or the (mean) curvature map for better representation of the surfaces or maps. Most of the time these maps are sparse and the Zernike fitting represents the complete Cartesian representation of these maps for display purposes or further analysis.

In block 614, the generated Cartesian epithelial thickness map or a further analysis thereof is stored in a data store (e.g., the data store 914 shown in FIG. 9) for future reference, access, and/or retrieval, or provided for display to a user on a display, such as the display (e.g., the display 122 (FIG. 1) or the optional display 910 (FIG. 9).

Motion-Corrected Epithelial Thickness Maps

In some embodiments, the motion-corrected model of the cornea, discussed above with respect to method 200, can be used to generate motion-artifact free epithelial thickness maps. When generating the maps, both the anterior and Bowman layers can be identified using the motion-corrected corneal image dataset as discussed above. In some embodiments, two surfaces can be reconstructed from the anterior and the outer edge of the Bowman's layers using higher order of the Zernike fitting (in the case of redial or sparse scans). Then a complete thickness map can be reconstructed by calculating the distance between the two surfaces using a distance transform method. This method gives accurate pointwise distances between two surfaces in three dimensions. The corneal motion correction is essential for three-dimensional thickness map reconstruction.

Figure 8A:
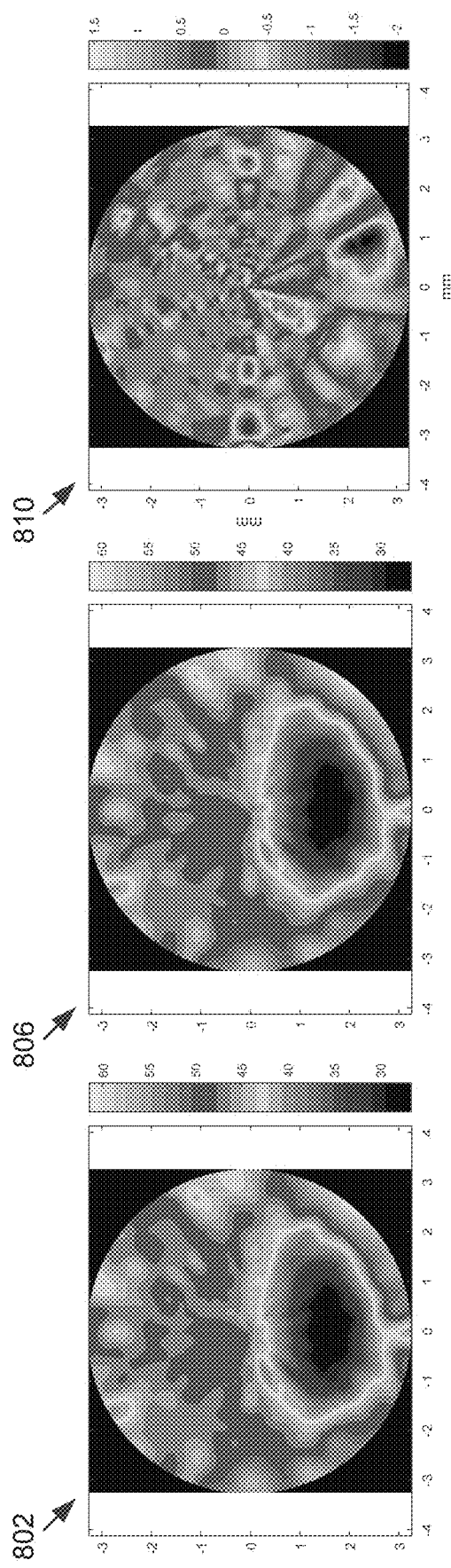
FIGS. 8A and 8B are two examples showing the significance of corneal motion correction prior to epithelial thickness mapping.
Figure 8B:
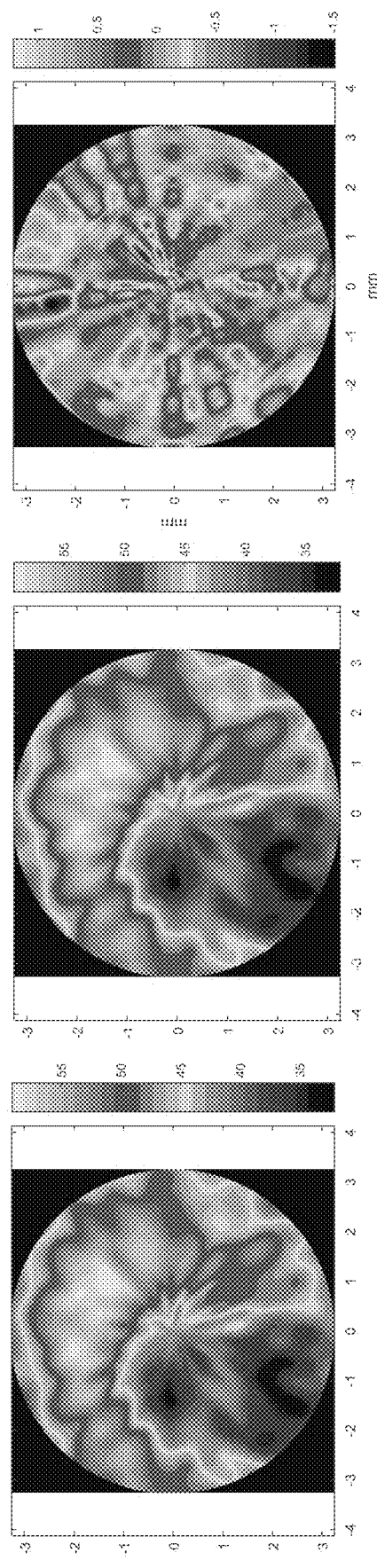

FIGS. 8A and 8B are two examples showing the significance of corneal motion correction prior to epithelial thickness mapping. The left images 802 and 804 represent the epithelial thickness map before motion correction, the middle images 806 and 808 represent the map after motion correction, and the right images 810 and 812 represent the difference map between before and after motion correction. A maximum error of +/−2 microns has been shown in these two examples which corresponds to 4% error if the average epithelial thickness of normal cases is assumed to be around 50 microns. This might be significant for refractive applications. The error increases as the motion gets larger.

Example Computer System

The processing unit 121 that has been discussed herein in reference to FIG. 1 can be implemented with a computer system configured to perform the functions described for this unit. For instance, the processing unit 121 can be implemented with the computer system 900, as shown in FIG. 9. The computer system 900 may include one or more processors 902, one or more memories 904, a communication unit 908, an optional display 910, one or more input devices 912, and a data store 914. The display 910 is shown with dotted lines to indicate it is an optional component, which, in some instances, may not be a part of the computer system 900. In some embodiments, the display 910 discussed herein is the display 122 that has been discussed with respect to FIG. 1.

The components 902, 904, 908, 910, 912, and 914 are communicatively coupled via a communication or system bus 916. The bus 916 can include a conventional communication bus for transferring data between components of a computing device or between computing devices. It should be understood that the computing system 900 described herein is not limited to these components and may include various operating systems, sensors, video processing components, input/output ports, user interface devices (e.g., keyboards, pointing devices, displays, microphones, sound reproduction systems, and/or touch screens), additional processors, and other physical configurations.

The processor(s) 902 may execute various hardware and/or software logic, such as software instructions, by performing various input/output, logical, and/or mathematical operations. The processor(s) 902 may have various computing architectures to process data signals including, for example, a complex instruction set computer (CISC) architecture, a reduced instruction set computer (RISC) architecture, and/or architecture implementing a combination of instruction sets. The processor(s) 902 may be physical and/or virtual, and may include a single core or plurality of processing units and/or cores. In some embodiments, the processor(s) 902 may be capable of generating and providing electronic display signals to a display device, such as the display 910, supporting the display of images, capturing and transmitting images, performing complex tasks including various types of feature extraction and sampling, etc. In some embodiments, the processor(s) 902 may be coupled to the memory(ies) 904 via a data/communication bus to access data and instructions therefrom and store data therein. The bus 916 may couple the processor(s) 902 to the other components of the computer system 900, for example, the memory(ies) 904, the communication unit 908, or the data store 914.

The memory(ies) 904 may store instructions and/or data that may be executed by the processor(s) 902. In the depicted embodiment, the memory(ies) 904 stores at least a motion correction module 905, a thickness map generation module 906, and a scan quality assessment module 907, each of which may include software, code, logic, or routines for performing any and/or all of the functionalities discussed herein. For instance, the motion correction module 905 may perform all or some of the steps of the method 200 depicted in FIG. 2A, the thickness map generation module 906 may perform all or some of the steps of the method 600 depicted in FIG. 6, and the scan quality assessment module 907 may perform all or some of the steps of the methods 220 and 250 depicted in FIGS. 2B-D. In some embodiments, the memory(ies) 904 may also be capable of storing other instructions and data including, for example, an operating system, hardware drivers, other software applications, databases, etc. The memory(ies) 904 are coupled to the bus 916 for communication with the processor(s) 902 and other components of the computer system 900. The memory(ies) 904 may include a non-transitory computer-usable (e.g., readable, writeable, etc.) medium, which can be any apparatus or device that can contain, store, communicate, propagate or transport instructions, data, computer programs, software, code, routines, etc. for processing by or in connection with the processor(s) 902. A non-transitory computer-usable storage medium may include any and/or all computer-usable storage media. In some embodiments, the memory(ies) 904 may include volatile memory, non-volatile memory, or both. For example, the memory(ies) 904 may include a dynamic random access memory (DRAM) device, a static random access memory (SRAM) device, flash memory, a hard disk drive, a floppy disk drive, a CD ROM device, a DVD ROM device, a DVD RAM device, a DVD RW device, a flash memory device, or any other mass storage device known for storing instructions on a more permanent basis.

The computer system for the processing unit 121 may include one or more computers or processing units at the same or different locations. When at different locations, the computers may be configured to communicate with one another through a wired and/or wireless network communication system, such as the communication unit 908. The communication unit 908 may include network interface devices (I/F) for wired and wireless connectivity. For example, the communication unit 908 may include a CAT-type interface, USB interface, or SD interface, transceivers for sending and receiving signals using Wi-Fi™; Bluetooth®, or cellular communications for wireless communication, etc. The communication unit 908 can link the processor(s) 902 to a computer network that may in turn be coupled to other processing systems.

The display 910 represents any device equipped to display electronic images and data as described herein. The display 910 may be any of a conventional display device, monitor or screen, such as an organic light-emitting diode (OLED) display, a liquid crystal display (LCD). In some embodiments, the display 910 is a touch-screen display capable of receiving input from one or more fingers of a user. For example, the device 910 may be a capacitive touch-screen display capable of detecting and interpreting multiple points of contact with the display surface.

The input device(s) 912 are any devices for inputting data on the computer system 900. In some embodiments, an input device is a touch-screen display capable of receiving input from one or more fingers of the user. The functionality of the input device(s) 912 and the display 910 may be integrated, and a user of the computer system 900 may interact with the system by contacting a surface of the display 910 using one or more fingers. In other embodiments, an input device is a separate peripheral device or combination of devices. For example, the input device(s) 912 may include a keyboard (e.g., a QWERTY keyboard) and a pointing device (e.g., a mouse or touchpad). The input device(s) 912 may also include a microphone, a web camera, or other similar audio or video capture devices.

The data store 914 can be an information source capable of storing and providing access to data. In the depicted embodiment, the data store 914 is coupled for communication with the components 902, 904, 908, 910, and 912 of the computer system 900 via the bus 916, and coupled, via the processor(s) 902, for communication with the motion correction module 905, the thickness map generation module 906, and the scan quality assessment module 907. In some embodiments, each of the motion correction module 905, the thickness map generation module 906, and the scan quality assessment module 907 is configured to manipulate, i.e., store, query, update, and/or delete, data stored in the data store 914 using programmatic operations.

In the above description, for purposes of explanation, numerous specific details are set forth in order to provide a thorough understanding of the specification. It should be apparent, however, that the subject matter of the present application can be practiced without these specific details. It should be understood that the reference in the specification to "one embodiment", "some embodiments", or "an embodiment" means that a particular feature, structure, or characteristic described in connection with the embodiment is included in one or more embodiments of the description. The appearances of the phrase "in one embodiment" or "in some embodiments" in various places in the specification are not necessarily all referring to the same embodiment(s).

Furthermore, the description can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

The foregoing description of the embodiments of the present subject matter has been presented for the purposes of illustration and description. It is not intended to be exhaustive or to limit the present embodiment of subject matter to the precise form disclosed. Many modifications and variations are possible in light of the above teaching. It is intended that the scope of the present embodiment of subject matter be limited not by this detailed description, but rather by the claims of this application. As will be understood by those familiar with the art, the present subject matter may be embodied in other specific forms without departing from the spirit or essential characteristics thereof. Furthermore, it should be understood that the modules, routines, features, attributes, methodologies and other aspects of the present subject matter can be implemented using hardware, firmware, software, or any combination of the three.

I claim:

1. A method comprising:
   collecting, by an optical coherence tomography (OCT) system, a set of B-scans over a range of different transverse locations on the cornea of the eye;
   segmenting, by the OCT system, a B-scan of the set of B-scans to identify an anterior corneal layer and an outer edge of a Bowman's layer in the B-scan;
   applying, by the OCT system, an average filtering process in a lateral direction of an axial gradient to enhance the outer edge of the Bowman's layer;
   calculating, by the OCT system, a thickness value for the B-scan by computing a distance from the anterior corneal layer to the outer edge of a Bowman's layer;
   combining, by the OCT system, the thickness values from the multiple B-scans to create a polar epithelial thickness map;
   converting, by the OCT system, the polar epithelial thickness map to a Cartesian epithelial thickness map using a fitting method; and
   at least one of storing or displaying, by the OCT system, the Cartesian epithelial thickness map or information derived from the Cartesian epithelial thickness map.

2. The method of claim 1, wherein the fitting method is comprising at least one of a Zernike fitting method, or a grid fitting method.

3. The method of claim 1, further comprising, prior to computing the thickness value for the B-scan, performing, by the OCT system, one or more tests of scan quality to assess a scan quality of the B-scan based on a set of results associated with the segmenting of the B-scan.

4. The method of claim 1, further comprising downsampling by the OCT system, by one or more factors, in the lateral direction to reduce a size of the B-scan to enable enhanced estimation of a region of interest at transverse locations on the cornea of the eye.

5. The method of claim 1, wherein the collecting of one or more B-scans from the set of B-scans is performed from transverse locations that are distinct on the cornea of the eye.

6. The method of claim 5, wherein the transverse locations are used by the OCT system to generate a two-dimension image of the cornea of the eye.

7. The method of claim 1, wherein the collecting of the set of B-scans is performed by a single operative scan by the OCT system.

8. The method of claim 2, further comprising enabling, by the OCT system, configuring of a Bowman's layer based on a weak signal received by the OCT system from one or more peripheral regions of a corneal surface.

9. The method of claim 1, further comprising differentiating, by the OCT system, an anterior surface of a stroma of the eye that is in close proximity to the Bowman's layer of the cornea of the eye.

10. The method of claim 8, wherein the segmenting is configured by assignment of costs at a pixel level of a region of interest of the cornea of the eye.

11. The method of claim 10, wherein the Zernike fitting method is applied to a corneal surface of the region of interest of the cornea of the eye.

12. A non-transitory machine-readable storage medium that provides instructions that, if executed by a processor, are configurable to cause the processor to perform operations comprising:
   collecting a set of B-scans over a range of one or more different transverse locations on a cornea of an eye;
   segmenting a B-scan of the set of B-scans to identify an anterior corneal layer and an outer edge of a Bowman's layer in the B-scan;
   applying a filtering process to an axial gradient associated with the outer edge of the Bowman's layer for enhancing the outer edge of the Bowman's layer;
   calculating a thickness value for the B-scan by computing a distance from the anterior corneal layer to the outer edge of the Bowman's layer;
   combining at least one thickness value from the B-scan to create a polar epithelial thickness map;

converting the polar epithelial thickness map to a cartesian epithelial thickness map using a fitting method; and at least one of storing or displaying, the cartesian epithelial thickness map or information derived from the cartesian epithelial thickness map.

13. The medium of claim 12, further comprising applying the fitting method that comprises at least one of a Zernike fitting method, or a grid fitting method.

14. The medium of claim 12, comprising, prior to computing at least one thickness value for the B-scan, performing one or more tests of scan quality to assess a scan quality of the B-scan based on results of the segmenting of the B-scan.

15. The medium of claim 12, further comprising downsampling by one or more factors, in a lateral direction to reduce a size of a B-scan to enable enhanced estimation of a region of interest about transverse locations on the cornea of the eye.

16. The medium of claim 12, further comprising collecting at least one B-scan of the set of B-scans from one or more distinct transverse locations of the cornea of the eye to form the polar epithelial thickness map.

17. The medium of claim 12, further comprising enabling a single scan to collect the set of B-scans over the range of different transverse locations on a cornea of an eye to form the polar epithelial thickness map.

18. The medium of claim 12, further comprising defining the Bowman's layer based on a weak signal at one or more peripheral regions of a transverse location of the cornea of the eye to form the polar epithelial thickness map.

19. The medium of claim 12, further comprising delineating the Bowman's layer from an anterior surface of a stroma of the eye that is within a close proximity to the Bowman's layer when displaying the cartesian epithelial thickness map.

20. The medium of claim 12, further comprising segmenting by assigning a cost function in accordance with a pixel level of a region of interest.

21. The medium of claim 13, further comprising applying the Zernike fitting method to one or more corneal surfaces to form the polar epithelial thickness map.

22. An apparatus comprising:

a processor;

a memory storing a computer program, the memory in communication with the processor and the processor configured to:

collect a set of B-scans at transverse locations that are selected on a cornea of an eye;

segment a B-scan of the set of B-scans to identify an anterior corneal layer and an outer edge of a Bowman's layer of at least one B-scan;

apply an imaging filtering technique to improve in visibility the outer edge of the Bowman's layer;

calculate at least one thickness value for the B-scan by computing a distance from the anterior corneal layer to the outer edge of the Bowman's layer;

combine the thickness value from one or more B-scans to create a polar epithelial thickness map;

convert the polar epithelial thickness map to a cartesian epithelial thickness map using a fitting method; and at least one of store or display the cartesian epithelial thickness map or information derived from the cartesian epithelial thickness map.

* * * * *